(12) United States Patent
Mayer et al.

(10) Patent No.: US 9,053,454 B2
(45) Date of Patent: Jun. 9, 2015

(54) AUTOMATED STRAIGHT-THROUGH PROCESSING IN AN ELECTRONIC DISCOVERY SYSTEM

(75) Inventors: Michael J. Mayer, Charlotte, NC (US); Hayden S. Johnson, Jacksonville, FL (US); Jay A. Johnson, Jacksonville, FL (US); Emerson D. Miller, Charlotte, NC (US); Christopher D. Montrois, Jacksonville, FL (US); Brian L. Toomey, Charlotte, NC (US)

(73) Assignee: BANK OF AMERICA CORPORATION, Charlotte, NC (US)

( * ) Notice: Subject to any disclaimer, the term of this patent is extended or adjusted under 35 U.S.C. 154(b) by 382 days.

(21) Appl. No.: 12/846,590

(22) Filed: Jul. 29, 2010

(65) Prior Publication Data

US 2011/0131225 A1 Jun. 2, 2011

Related U.S. Application Data

(63) Continuation-in-part of application No. 12/627,791, filed on Nov. 30, 2009, now Pat. No. 8,364,681.

(51) Int. Cl.
*G06F 7/00* (2006.01)
*G06Q 10/10* (2012.01)
(Continued)

(52) U.S. Cl.
CPC .............. *G06Q 10/10* (2013.01); *G06F 19/24* (2013.01); *G06Q 10/06* (2013.01)

(58) Field of Classification Search
USPC ........................................................ 707/609
See application file for complete search history.

(56) References Cited

U.S. PATENT DOCUMENTS 5,497,317 A   3/1996   Hawkins et al.
6,119,137 A   9/2000   Smith et al.
(Continued)

FOREIGN PATENT DOCUMENTS

EP   1093068 A2   4/2001
EP   1349089 A2   1/2003
(Continued)

OTHER PUBLICATIONS

Ciravegna et al.: "User-System Cooperation in Document Annotation based on Information Extraction" 2002. Proceedings of the 13th International Conference on Knowledge Engineering and Knowledge Management.
(Continued)

*Primary Examiner* — Hosain Alam
*Assistant Examiner* — Eliyah S Harper
(74) *Attorney, Agent, or Firm* — Michael A. Springs; Moore & Van Allen PLLC; James C. Edwards

(57) ABSTRACT

Embodiments of the invention relate to systems, methods, and computer program products for automated straight-through processing in an electronic discovery system. Further, the embodiments described herein provide for electronic discovery processes, such as, but not limited to, data collection, barcoding, source-to-processing, quality control, third-party network data transfer and data analysis platform loading to be automatically initiated and performed in pipeline fashion. Once a process is completed on a dataset, the next process in the flow is automatically initiated unless exceptions are determined to exist. In addition, embodiments provide for prioritizing cases and conducting each process in the straight-through data processing based on the case prioritization.

18 Claims, 20 Drawing Sheets

(51) Int. Cl.
*G06Q 10/06* (2012.01)
*G06F 19/24* (2011.01)

(56) References Cited

U.S. PATENT DOCUMENTS

| | | |
|---|---|---|
| 6,601,108 B1 | 7/2003 | Marmor |
| 6,658,625 B1 | 12/2003 | Allen |
| 6,941,361 B1 | 9/2005 | Fink et al. |
| 7,076,543 B1 | 7/2006 | Kirti et al. |
| 7,080,073 B1* | 7/2006 | Jiang et al. .................. 1/1 |
| 7,124,249 B1 | 10/2006 | Darcy |
| 7,134,020 B2 | 11/2006 | Eagle et al. |
| 7,376,969 B1 | 5/2008 | Njemanze et al. |
| 7,451,103 B1 | 11/2008 | Boyle et al. |
| 7,451,139 B2 | 11/2008 | Namba |
| 7,765,181 B2 | 7/2010 | Thomas et al. |
| 7,895,200 B2* | 2/2011 | Baldovinos ............... 707/732 |
| 7,895,229 B1 | 2/2011 | Paknad |
| 8,073,729 B2 | 12/2011 | Kisin et al. |
| 8,265,925 B2* | 9/2012 | Aarskog .................... 704/9 |
| 2002/0194097 A1 | 12/2002 | Reitz |
| 2002/0198629 A1 | 12/2002 | Ellis |
| 2003/0154199 A1 | 8/2003 | Thomas et al. |
| 2003/0182375 A1 | 9/2003 | Zhu et al. |
| 2003/0200308 A1 | 10/2003 | Tameda et al. |
| 2004/0010515 A1* | 1/2004 | Sawafta .................... 707/104.1 |
| 2004/0098424 A1 | 5/2004 | Seidenberg et al. |
| 2004/0230572 A1* | 11/2004 | Omoigui ................... 707/3 |
| 2004/0260733 A1 | 12/2004 | Adelstein et al. |
| 2005/0086720 A1 | 4/2005 | Shimizu et al. |
| 2005/0152235 A1 | 7/2005 | Hoshizawa |
| 2005/0177527 A1* | 8/2005 | Morris et al. ............ 705/400 |
| 2005/0193028 A1* | 9/2005 | Oswalt ...................... 707/200 |
| 2005/0278362 A1* | 12/2005 | Maren et al. .............. 707/100 |
| 2006/0095795 A1 | 5/2006 | Nakamura et al. |
| 2006/0167877 A1* | 7/2006 | Lee et al. ................... 707/7 |
| 2006/0256739 A1 | 11/2006 | Seier et al. |
| 2007/0027851 A1* | 2/2007 | Kruy et al. ................ 707/3 |
| 2007/0027974 A1 | 2/2007 | Lee et al. |
| 2007/0073894 A1 | 3/2007 | Erickson et al. |
| 2007/0088754 A1 | 4/2007 | Brannon et al. |
| 2007/0112783 A1 | 5/2007 | McCreight et al. |
| 2007/0162547 A1 | 7/2007 | Ross |
| 2007/0208918 A1 | 9/2007 | Harbin et al. |
| 2007/0226170 A1 | 9/2007 | Sun |
| 2007/0271517 A1 | 11/2007 | Finkelman et al. |
| 2007/0288579 A1 | 12/2007 | Schunemann |
| 2008/0027895 A1 | 1/2008 | Combaz |
| 2008/0046260 A1 | 2/2008 | Ghielmetti et al. |
| 2008/0061146 A1 | 3/2008 | Komaki |
| 2008/0071726 A1* | 3/2008 | Nair et al. ................. 707/1 |
| 2008/0082672 A1 | 4/2008 | Garrett |
| 2008/0115082 A1* | 5/2008 | Simmons et al. .......... 715/804 |
| 2008/0168145 A1 | 7/2008 | Wilson |
| 2008/0252936 A1 | 10/2008 | Stratton |
| 2008/0288479 A1 | 11/2008 | Paknad et al. |
| 2008/0294492 A1 | 11/2008 | Simpson et al. |
| 2009/0001162 A1 | 1/2009 | Asher et al. |
| 2009/0006973 A1 | 1/2009 | Newell et al. |
| 2009/0043819 A1 | 2/2009 | Searl et al. |
| 2009/0132262 A1 | 5/2009 | Paknad |
| 2009/0164522 A1 | 6/2009 | Fahey |
| 2009/0165026 A1 | 6/2009 | Paknad et al. |
| 2009/0183253 A1 | 7/2009 | Kates |
| 2009/0286219 A1 | 11/2009 | Kisin et al. |
| 2009/0287685 A1* | 11/2009 | Charnock et al. ......... 707/5 |
| 2010/0017239 A1 | 1/2010 | Saltzman et al. |
| 2010/0033750 A1 | 2/2010 | Tischler et al. |
| 2010/0082382 A1 | 4/2010 | Kisin et al. |
| 2010/0082555 A1 | 4/2010 | Ogawa et al. |
| 2010/0094848 A1* | 4/2010 | Reddy et al. ............. 707/705 |
| 2010/0205020 A1 | 8/2010 | Losey |
| 2010/0223108 A1 | 9/2010 | Quinn, Jr. |
| 2010/0274815 A1* | 10/2010 | Vanasco ................... 707/798 |
| 2011/0040600 A1 | 2/2011 | Paknad et al. |
| 2011/0173033 A1 | 7/2011 | Paknad et al. |

FOREIGN PATENT DOCUMENTS

| | | |
|---|---|---|
| WO | 01/27765 A1 | 4/2001 |
| WO | 0210967 A2 | 2/2002 |
| WO | WO 02/42952 A1 | 5/2002 |
| WO | 02071192 A2 | 9/2002 |
| WO | 03/065256 A1 | 8/2003 |
| WO | 2004092902 A2 | 10/2004 |
| WO | 2006001833 A2 | 1/2006 |
| WO | 2006031836 A2 | 3/2006 |
| WO | WO 2006/031836 A2 | 3/2006 |
| WO | 2006052441 A2 | 5/2006 |
| WO | 2007/044709 A2 | 4/2007 |
| WO | 2007076515 A2 | 7/2007 |
| WO | WO 2007/076515 | 7/2007 |
| WO | 2008009991 A1 | 1/2008 |
| WO | 2008070415 A2 | 6/2008 |
| WO | WO 2008/070415 A2 | 6/2008 |

OTHER PUBLICATIONS

Buchholz et al.: "On the Role of File System Metadata in Digital Forensics", Journal of Digital Investigation, vol. 1(4), pp. 297-308, Dec. 1, 2004.

Golden et al. Scalpel: "A Frugal, High Performance File Carver" 2005 Digital Forensic Research Workshop (DFRWS) New Orleans, LA.

Manson et al.: "Is the Open Way a Better Way? Digital Forensics using Open Source Tools". System Sciences, 2007. HICSS 2007. 40th Annual Hawaii International Conference On, IEEE, PI, Jan. 1, 2007. ISBN:978-0-7695-2755-0.

Berinato: "The Rise of Anti-Forensics" http/www.csoonline.com/article/print/221208. Jun. 8, 2007.

Anonymous: "EDRM LegalTech 2009 Luncheon Presentation" E.D. R.M. The Electronic Discovery Reference Model Feb. 9, 2009. Retrieved from the Internet: http://www.edrm.net/wp-content/plugins/download-monitor/download.php?id=6.

Singapore Patent Application No. 201002126-9 Search Report and Written Opinion mailed Aug. 3, 2011.

Singapore Patent Application No. 201002129-3 Search Report and Written Opinion mailed Aug. 3, 2011.

Singapore Patent Application No. 201002128-5 Search Report and Written Opinion mailed Aug. 3, 2011.

Singapore Patent Application No. 201002139-2 Search Report and Written Opinion mailed Aug. 3, 2011.

Singapore Patent Application No. 201002137-6 Search Report and Written Opinion mailed Aug. 15, 2011.

Singapore Patent Application No. 201002138-4 Search Report and Written Opinion mailed Aug. 19, 2011.

Singapore Patent Application No. 201002125-1 Search Report and Written Opinion mailed Aug. 24, 2011.

Singapore Patent Application No. 201002134-3 Search Report and Written Opinion mailed Aug. 25, 2011.

Singapore Patent Application No. 201002124-4 Search Report and Written Opinion mailed Aug. 25, 2011.

Search Report and Written Opinion for Divisional Singapore Patent Application No. 201304691-7 mailed Nov. 5, 2014.

European Patent Office. European Office Action dated Apr. 26, 2012. European Application No. 10 250 583.1. Name of Applicant: Bank of America Corporation. English Language. 10 pages.

SysTools Software, "Export Notes—Notes Email Migration Tool", 2008, available online: http://web.archive.org/web/20080201104418/http://www.exportlotusnotes.com/export-notes.

Process Text Group, "ABC Amber BlackBerry Converter", 2008, available online: http:web.archive.org/web/20080302025411/http://www.processtext.com/abcblackberry.html.

Search Report and Written Opinion for Singapore Application No. 201002122-8 mailed Jan. 3, 2012.

Search Report and Written Opinion for Singapore Application No. 201002141-8 mailed Jan. 3, 2012.

(56) References Cited

OTHER PUBLICATIONS

Search Report and Written Opinion for Singapore Application No. 201002143-4 mailed Jan. 3, 2012.
Search Report and Written Opinion for Singapore Application No. 201002120-2 mailed Feb. 10, 2012.
Second Written Opinion for Singapore Application No. 201002126-9 mailed Mar. 14, 2012.
Second Written Opinion for Singapore Application No. 201002128-5 mailed Mar. 14, 2012.
Second Written Opinion for Singapore Application No. 201002129-3 mailed Mar. 14, 2012.
Second Written Opinion for Singapore Application No. 201002139-2 mailed Mar. 14, 2012.
European Patent Office. European Office Action dated Apr. 26, 2012. European Application No. 10 250 585.6. Name of Applicant: Bank of America Corporation. English Language. 10 pages.
European Patent Office. European Office Action dated Apr. 26, 2012. European Application No. 10 250 589.8. Name of Applicant: Bank of America Corporation. English Language. 10 pages.
European Patent Office. European Office Action dated Apr. 26, 2012. European Application No. 10 250 579.9. Name of Applicant: Bank of America Corporation. English Language. 10 pages.
European Patent Office. European Office Action dated Apr. 26, 2012. European Application No. 10 250 584.9. Name of Applicant: Bank of America Corporation. English Language. 10 pages.
European Patent Office. European Office Action dated Apr. 25, 2012. European Application No. 10 250 586.4. Name of Applicant: Bank of America Corporation. English Language. 10 pages.
European Patent Office. European Office Action dated Apr. 25, 2012. European Application No. 10 250 581.5. Name of Applicant: Bank of America Corporation. English Language. 10 pages.
European Patent Office. European Office Action dated Apr. 25, 2012. European Application No. 10 250 576.5. Name of Applicant: Bank of America Corporation. English Language. 11 pages.
European Patent Office. European Office Action dated Apr. 27, 2012. European Application No. 10 250 587.2. Name of Applicant: Bank of America Corporation. English Language. 10 pages.
European Patent Office. European Office Action dated Apr. 25, 2012. European Application No. 10 250 577.3. Name of Applicant: Bank of America Corporation. English Language. 10 pages.
European Patent Office. European Office Action dated Apr. 25, 2012. European Application No. 10 250 580.7. Name of Applicant: Bank of America Corporation. English Language. 10 pages.
European Patent Office. European Office Action dated Apr. 25, 2012. European Application No. 10 250 590.6. Name of Applicant: Bank of America Corporation. English Language. 10 pages.
European Patent Office. European Office Action dated Apr. 26, 2012. European Application No. 10 250 582.3. Name of Applicant: Bank of America Corporation. English Language. 10 pages.
Great Britain Intellectual Property Office. GB Examination Report dated Apr. 23, 2012. Great Britain Application No. GB1108090.0. Name of Applicant: Bank of America Corporation. English Language. 3 pages.
Hewlett Packard. "*HP OpenView Storage Data Protector Concepts Guide.*" Release A.06.00. Manufacturing Part No. B6960-96001. English Language. Jul. 2006.
Hungarian Intellectual Property Office. Written Opinion mailed Apr. 5, 2012. Hungary Application No. 201002137-6. Name of Applicant: Bank of America Corporation. English Language. 8 pages. Date of Written Opinion: Mar. 21, 2012.
Hungarian Intellectual Property Office. Written Opinion mailed Apr. 5, 2012. Hungary Application No. 201002138-4. Name of Applicant: Bank of America Corporation. English Language. 8 pages. Date of Written Opinion: Mar. 29, 2012.
European Patent Office. European Office Action dated Apr. 25, 2012. European Application No. 10 250 578.1. Name of Applicant: Bank of America Corporation. English Language. 10 pages.
European Patent Office. European Office Action dated Apr. 25, 2012. European Application No. 10 250 591.4. Name of Applicant: Bank of America Corporation. English Language. 10 pages.
Examination Report for European Application No. 10250588.0 dated Jun. 27, 2012.
Second Written Opinion for Singapore Application No. 201002120-2 dated Jul. 20, 2012.
Second Written Opinion for Singapore Application No. 201002141-8 dated Jul. 20, 2012.
Second Written Opinion for Singapore Application No. 201002140-0 dated Aug. 6, 2012.
Second Written Opinion for Singapore Application No. 201002144-2 dated Aug. 6, 2012.
Singapore Patent Application No. 201002142-6 Search Report and Written Opinion mailed Sep. 5, 2011.
Singapore Patent Application No. 201002144-2 Search Report and Written Opinion mailed Sep. 5, 2011.
Singapore Patent Application No. 201002140-0 Search Report and Written Opinion mailed Sep. 27, 2011.
J. Barlow, L. Bean and D.D. Hott: "Employee 'Spy' Software: Should You Use It?" The Journal of Corporate Accounting & Finance, Document No. XP-002601405, pages 7-12; Retrieved from the Internet: URL: http://onlinelibrary. wiley.com/10.1002/icaf.10162/abstract [retreived on Sep. 17, 2010].
Dan Manson et al.: "Is the Open Way a Better Way? Digital Forensics using Open Source Tools", Proceedings of the 40th Hawaii International Conference on System Sciences—2007 [dated Jan. 1, 2007]; 10 pages total.
Anonymous: "EDRM LegalTech 2009 Luncheon Presentation", E.D.R.M.—The Electronic Discovery Reference Model; Document No. XP-002601404 LegalTech Lunch & Learn, Feb. 3, 2009, LegalTech New York; Retrieved from the Internet: URL:http//edrm.net/002/wp-content/uploads/2009/09/EDRM_LegalTech.pdf [retrieved Sep. 17, 2010].
Danish Patent and Trademark Office. Singapore Examination Report mailed Mar. 15, 2012. Applicant: Bank of America Corporation. Singapore Patent Application No. 201002134-3. DKPTO SE No. SE 2012 00392v. English Language. 10 pages. Mar. 12, 2012.
Danish Patent and Trademark Office. Singapore Examination Report mailed Mar. 15, 2012. Applicant: Bank of America Corporation. Singapore Patent Application No. 201002124-4. DKPTO SE No. SE 2012 00392y. English Language. 10 pages. Date of Examination Report: Mar. 12, 2012.

* cited by examiner

| | Barcode | Collection Date | Start / From Date | Case # | This Case? | PE? | ED? | Start / Files |
|---|---|---|---|---|---|---|---|---|
| ☐ | xxxxxx | 5/22/2008 12:20:07 PM | | xxxxx | | | | 1 files |
| ☐ | xxxxxx | 6/19/2008 2:23:21 PM | | xxxxx | | | | 1(123 MB) files |
| ☐ | xxxxxx | 6/19/2008 2:35:11 PM | | xxxxx | | | | 1(123 MB) files |
| ☐ | xxxxxx | 8/14/2008 11:59:25 AM | | xxxxx | | | | 1(160 MB) files |
| ☐ | xxxxxx | 11/14/2008 1:31:17 PM | | xxxxx | | | | 1(236 MB) files |
| ☑ | xxxxxx | 12/11/2008 2:07:03 PM | | xxxxx | Y | | | 1(232 MB) files |
| ☐ | xxxxxx | | | xxxxx | | | | 9(40 MB) files |
| ☐ | xxxxxx | | | xxxxx | | | | 230(64 MB) files |
| ☐ | xxxxxx | 6/19/2008 1:53:52 PM | | xxxxx | | | | 9(40 MB) files |
| ☐ | xxxxxx | 8/14/2008 11:50:27 AM | | xxxxx | | | | 9(40 MB) files |
| ☐ | xxxxxx | 10/16/2008 12:54:06 PM | | xxxxx | | | | 9(40 MB) files |
| ☐ | xxxxxx | 10/16/2008 12:54:06 PM | | xxxxx | | | | 9(40 MB) files |
| ☐ | xxxxxx | 10/24/2008 8:44:47 AM | | xxxxx | | | | 9(40 MB) files |
| ☐ | xxxxxx | 11/14/2008 1:24:36 PM | | xxxxx | | | | 9(40 MB) files |
| ☐ | xxxxxx | 8/14/2008 11:50:27 AM | | xxxxx | | | | 366(190 MB) files |
| ☐ | xxxxxx | 10/16/2008 12:54:06 PM | | xxxxx | | | | 400(183 MB) files |
| ☐ | xxxxxx | 10/16/2008 12:54:06 PM | | xxxxx | | | | 400(183 MB) files |

AUTOMATED STRAIGHT-THROUGH PROCESSING IN AN ELECTRONIC DISCOVERY SYSTEM

REFERENCE TO CO-PENDING APPLICATION FOR PATENT

The present application is a continuation-in-part of U.S. patent application Ser. No. 12/627,791, entitled, "Electronic Discovery System," filed on Nov. 30, 2009 now U.S. Pat. No. 8,364,681, assigned to the assignee of the present application, the contents of which are hereby incorporated by reference in their entirety.

FIELD

In general, embodiments of the invention relate to methods, systems and computer program products for electronic discovery and, more particularly, automated straight-through processing in an electronic discovery system.

BACKGROUND

Electronic discovery, commonly referred to as e-discovery or eDiscovery, refers to any process in which electronic data is sought, located, secured and searched with the intent of using it as evidence in a legal proceeding, an audit, a regulatory investigation, a forensics investigation or the like. E-discovery can be carried out offline on a particular computer or it can be accomplished in a network environment.

The nature of digital data makes it extremely well-suited for investigation. In particular, digital data can be electronically searched with ease, while paper documents must be scrutinized manually. Furthermore, it is difficult or impossible to completely destroy digital data, particularly if the data is stored in a network environment. This is because the data appears on multiple hard drives, and because digital files, even if deleted, generally can be undeleted. In fact, the only reliable means of destroying digital data is to physically destroy any and all hard drives where it is stored.

In the process of electronic discovery, data of all types can serve as evidence. This can include text, image, calendar event data, databases, spreadsheets, audio files, multimedia files, web sites and computer programs. Electronic mail (i.e., e-mail) can be an especially valuable source of evidence in civil or criminal litigation, because people are often less careful in these exchanges than in hard copy correspondence such as written memos or postal letters. Certain regulations and other business needs require email to be retained for years.

E-discovery is an evolving field that goes far beyond mere technology. It gives rise to multiple issues, many of which have yet to be resolved. For example, identifying data required to satisfy a given discovery request, locating the appropriate set of data that has been identified, and retrieving the data once it has been identified and located all pose problems in and of themselves. This is especially evident if the data that is being identified, located and retrieved comes from an evolving or disparate enterprise, such as a corporation that has experienced mergers, acquisitions, downsizing and the like. Mergers and acquisitions mean that the technology infrastructure across the enterprise may vary, at least in the interim. However, e-discovery must be able locate and retrieve data from these disparate technology infrastructure in a timely fashion, sometimes within days of when the merger/acquisition occurs.

In addition to identifying, locating and retrieving digital data, the most critical part of any electronic discovery is the preservation of data, which involves maintaining an original source copy and storing it for preservation purposes or furthering processing. This too becomes a daunting task for the enterprise system that encompasses a myriad of different technology infrastructures and the like. Therefore, a need exists to improve the identification, location, retrieval and preservation processes, especially in instances in which the enterprise system includes disparate technology infrastructures and the like.

As previously noted, e-discovery, as opposed as conventional discovery of printed materials, provides for the ability to filter or search the data so as to reduce the volume of data to only that which is relevant to the request. Such searching is typically accomplished by determining a specific date range for the request, providing key words relevant to the case and the like. Searches using conceptual concepts, heuristics, linguistics and other variants are also becoming common. Still though, improvements in the area of searching are greatly in need to further add efficiency to the overall e-discovery process.

Once data has been retrieved, preserved and, in some instances, searched the electronic data may be reviewed by the requesting entity, such as a law firm, securities commission or the like. While large requests are generally suited for online review, the manner in which the data is presented for review adds efficiency to the review process and ultimately drives the cost of the review process. Therefore, improvements in the manner in which data is presented for review are also desirable as a means of increasing efficiency and reducing costs.

Lastly, once the digital data has been reviewed, data identified as relevant may need to be produced in a tangible format for further analysis or legal evidentiary purposes. The produced documents must be properly identified and include necessary redactions and confidentiality markings.

Currently, most e-discovery processing has been conducted manually or, in instances in which automated processing has been conducted, manual actions have been required to initiate the next step in the process. For example, processes such as, data collection, barcoding of data, source-to-processing functionality, quality control checks, third-party network data transfer and data analysis platform loading have, in-part or in whole, required case analyst intervention in order to complete the process. Such manual processing is inefficient, in that, invariably, time is lost waiting for a case analyst or someone else tasked to perform a function to perform the requisite action.

Therefore, a need exists to develop an automated system for processing of data in an electronic discovery system. The desired system should minimize case analyst or other associate intervention, such that case analyst or other associate intervention is only required in the event that a process is unable to automatically continue. The desired process should assign tasks to services that are executed automatically and, based on completion of the tasks, look for the next decision point in the overall data processing flow and continue processing until an exception occurs in the process, which may require manual intervention. Such straight-through type processing significantly reduces the time necessary to process electronic discovery data and, significantly reduces the manpower requirements associated with a labor-intensive methodology.

SUMMARY

The following presents a simplified summary of one or more embodiments in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Thus, further details are provided below for systems, apparatus, methods and computer program products for automated straight-through processing in an electronic discovery system, in accordance with embodiments of the present invention. The embodiments described herein provide for electronic discovery processes, such as, but not necessarily limited to, data collection, barcoding, source-to-processing, quality control, third-party network data transfer and data analysis platform loading to be automatically performed in pipeline fashion. Thus, once a process is completed, the next process in the flow is automatically initiated unless exceptions, such as, missing information or the like, which may require manual intervention, are determined to exist. Thus, present embodiments provide for an efficient means of processing data in an electronic discovery system, whereby manual intervention is minimized.

In addition, embodiments provide for prioritizing cases and conducting each step in the straight-through data processing based on the case prioritization, such that, data processing associated with cases identified as being high-priority are performed on a next-available thread basis, while data processing associated with low or no priority cases are placed in a queue and performed on a first-in, first-out basis. As such, present embodiments ensure that data processing related to high-priority cases is expedited through the system.

A method for automatic straight-through data processing in an electronic discovery system defines first embodiments of the invention. The method includes receiving, at computing device, case-defining information for creating a case the electronic discovery system and receiving, at a computing device, a request for electronic data associated with the case. The method further includes initiating, via a computing device processor, automated straight-through processing of the electronic data based on the request.

In specific embodiments of the method initiating further includes initiating, via a computing device processor, one or more of, and in some embodiments all of, automated collection of the electronic data, automated barcoding of the electronic data, automated source-to-processing of the electronic data, automated quality control checks, automated transfer of data to a third-party network and/or automated loading of the data on an data analysis platform.

In other embodiments of the method, each of the processes initiated in the automated straight-through processing are prioritized based on case priority. As such, processing associated with cases that are deemed to be of high-priority is conducted prior to processing associated with cases that are deemed to be of lower-priority. The case priority may be based on one or more of case client, age of the case, monetary risk of the case, reputational risk of the case, and/or client-defined case categorization.

An apparatus for automated straight-through data processing in an electronic discovery system provides for second embodiments of the invention. The apparatus includes a computing processor including a memory and at least one processor. The apparatus further includes an electronic discovery data processing module stored in the memory and executable by the processor. The module is configured to initiate automated straight-through processing of electronic data associated with an electronic discovery case based on receipt of a request for the data.

In specific embodiments of the apparatus, the module includes one or more of, and in some embodiments all of, a data collection routine configured to automatically collect the electronic data, a barcoding routine configured to automatically barcode the electronic data, a source-to-processing routine configured to automatically perform source-to-processing functions, a quality control routine configured to automatically perform quality control checks, a third-party network data transfer routine configured to automatically transfer the data to a third-party network and/or a data loader routine configured to automatically load the electronic data on to a data analysis platform.

In further specific embodiments of the apparatus, the electronic discovery data processing module further includes a prioritization routine configured to automatically determine a priority, based on a case priority, for each of the processes conducted in the straight-through processing, such as automatically collecting data, automatically barcoding the data, automatically performing source-to-processing functions, automatically performing quality control checks, automatically transferring the data to a third-party network, and/or automatically loading the electronic data onto a data analysis platform. The case priority may be based on one or more of case client, age of the case, monetary risk of the case, reputational risk of the case, and/or client-defined case categorization.

A computer program product that includes a non-transitory computer-readable medium provides for third embodiments of the invention. The computer-readable medium includes a first set of codes for causing a computer to receive case-defining information for creating a case the electronic discovery system. The computer-readable medium additionally includes a second set of codes for causing a computer to receive a request for electronic data associated with the case. In addition, the computer-readable medium includes a third set of codes of causing a computer to initiate automated straight-through processing of the electronic data based on the request.

To the accomplishment of the foregoing and related ends, the one or more embodiments comprise the features hereinafter fully described and particularly pointed out in the claims. The following description and the annexed drawings set forth in detail certain illustrative features of the one or more embodiments. These features are indicative, however, of but a few of the various ways in which the principles of various embodiments may be employed, and this description is intended to include all such embodiments and their equivalents.

BRIEF DESCRIPTION OF THE DRAWINGS

Figure 1:
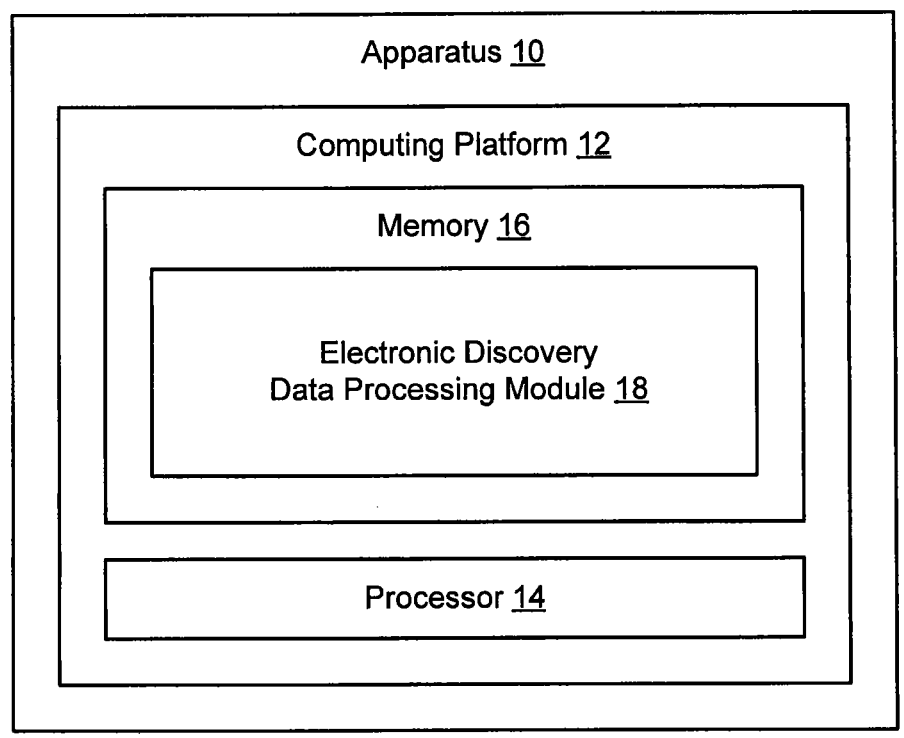
Figure 2:
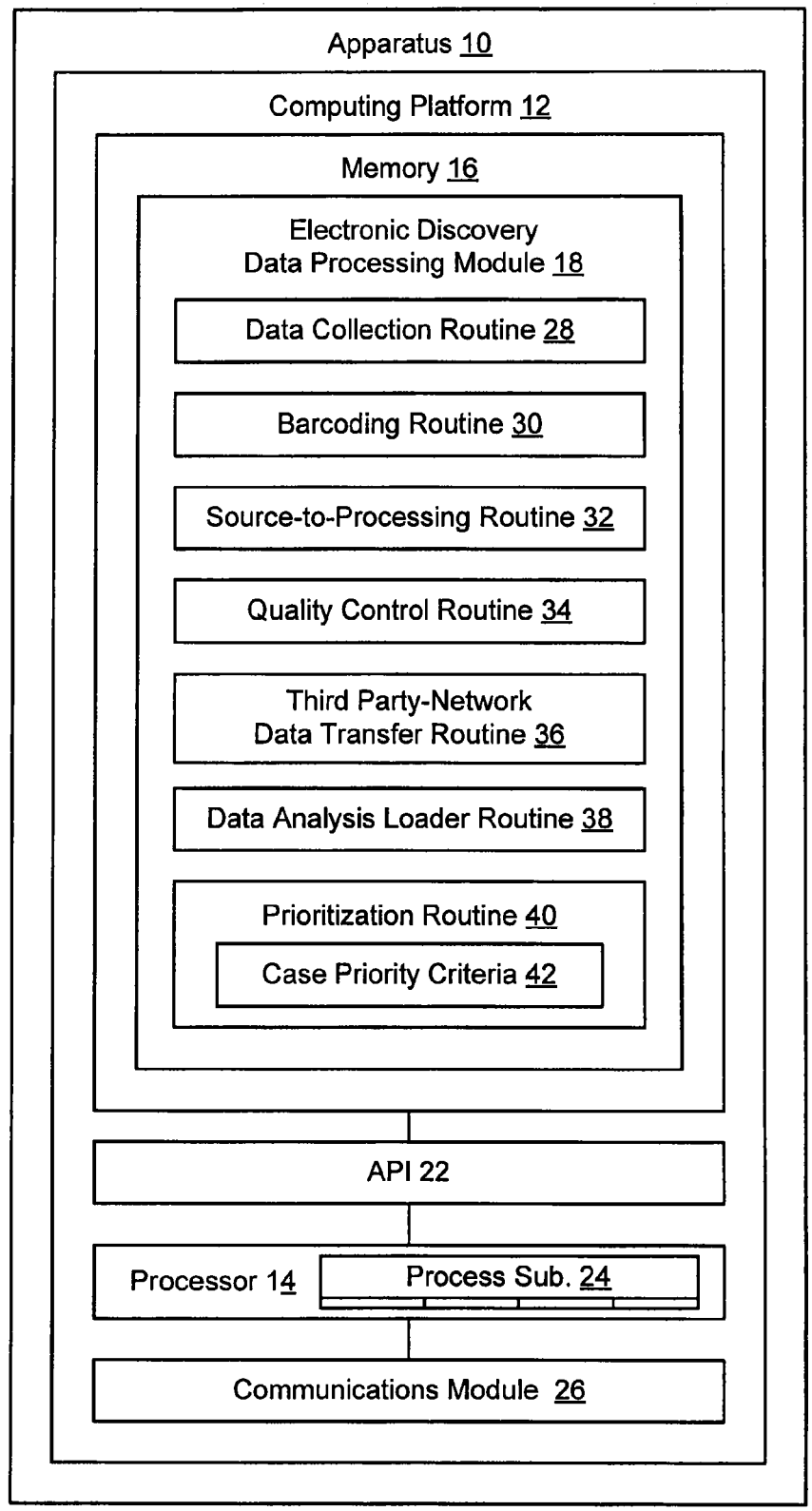
Figure 3:
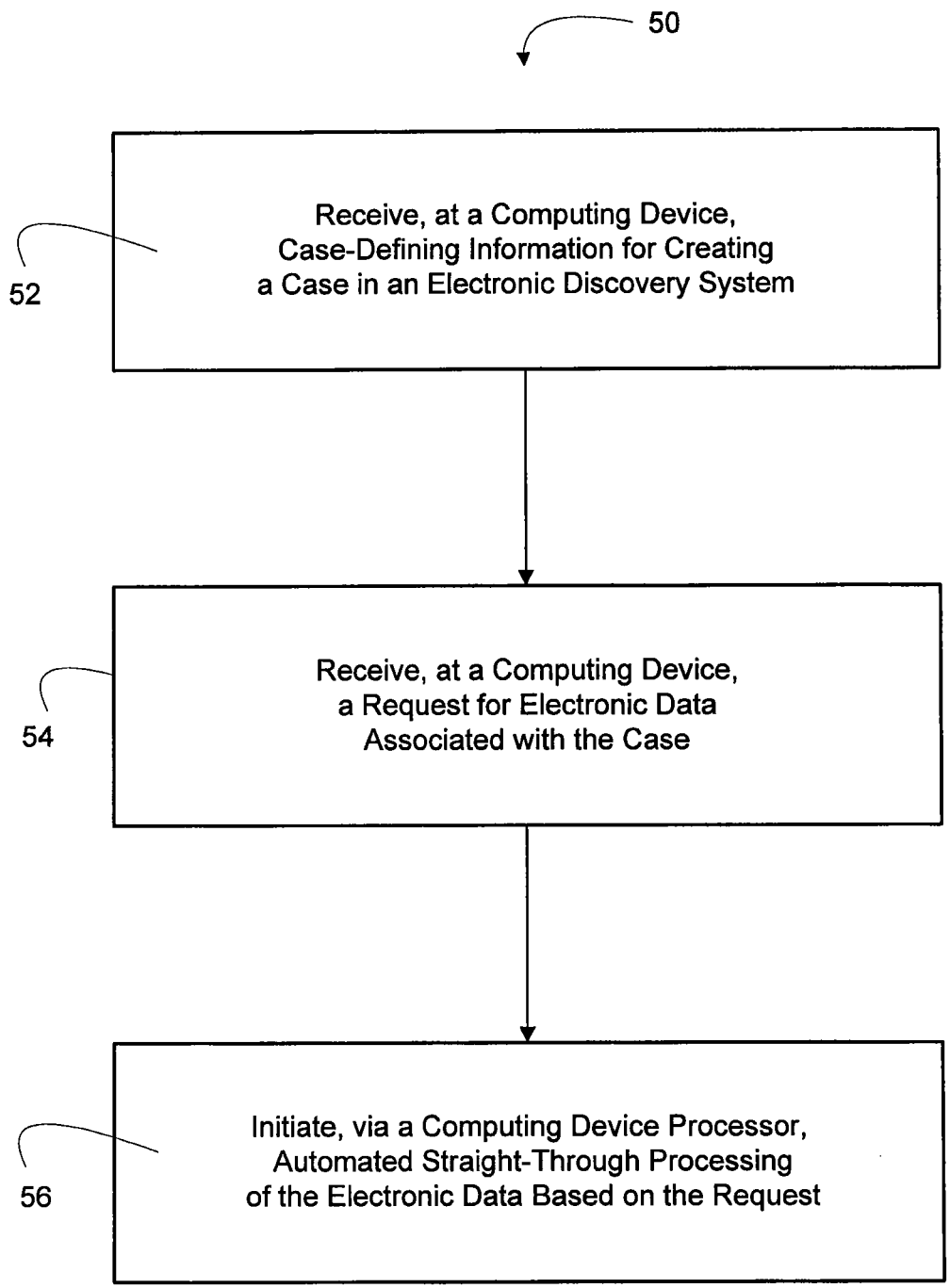
Figure 4:
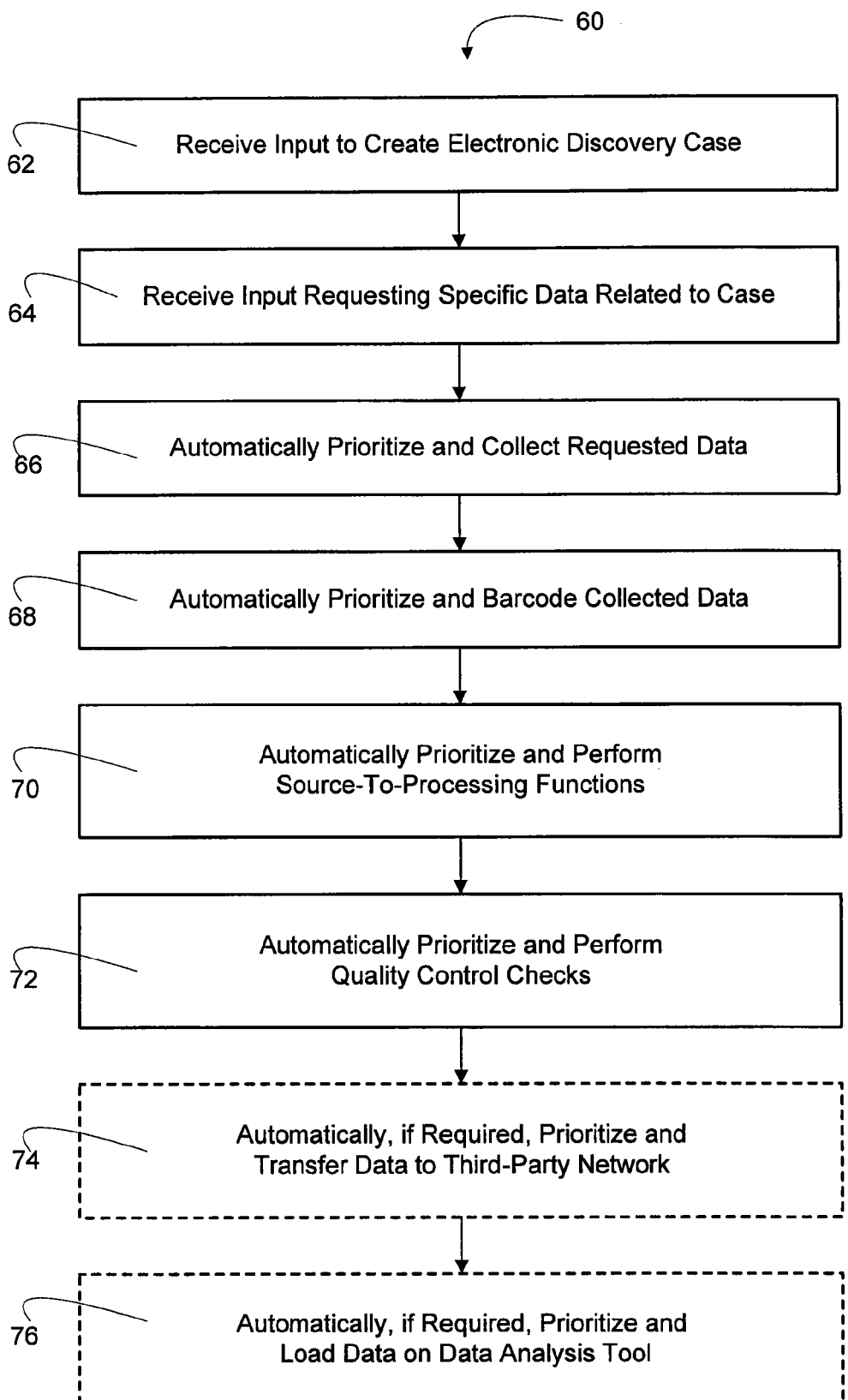
Figure 5:
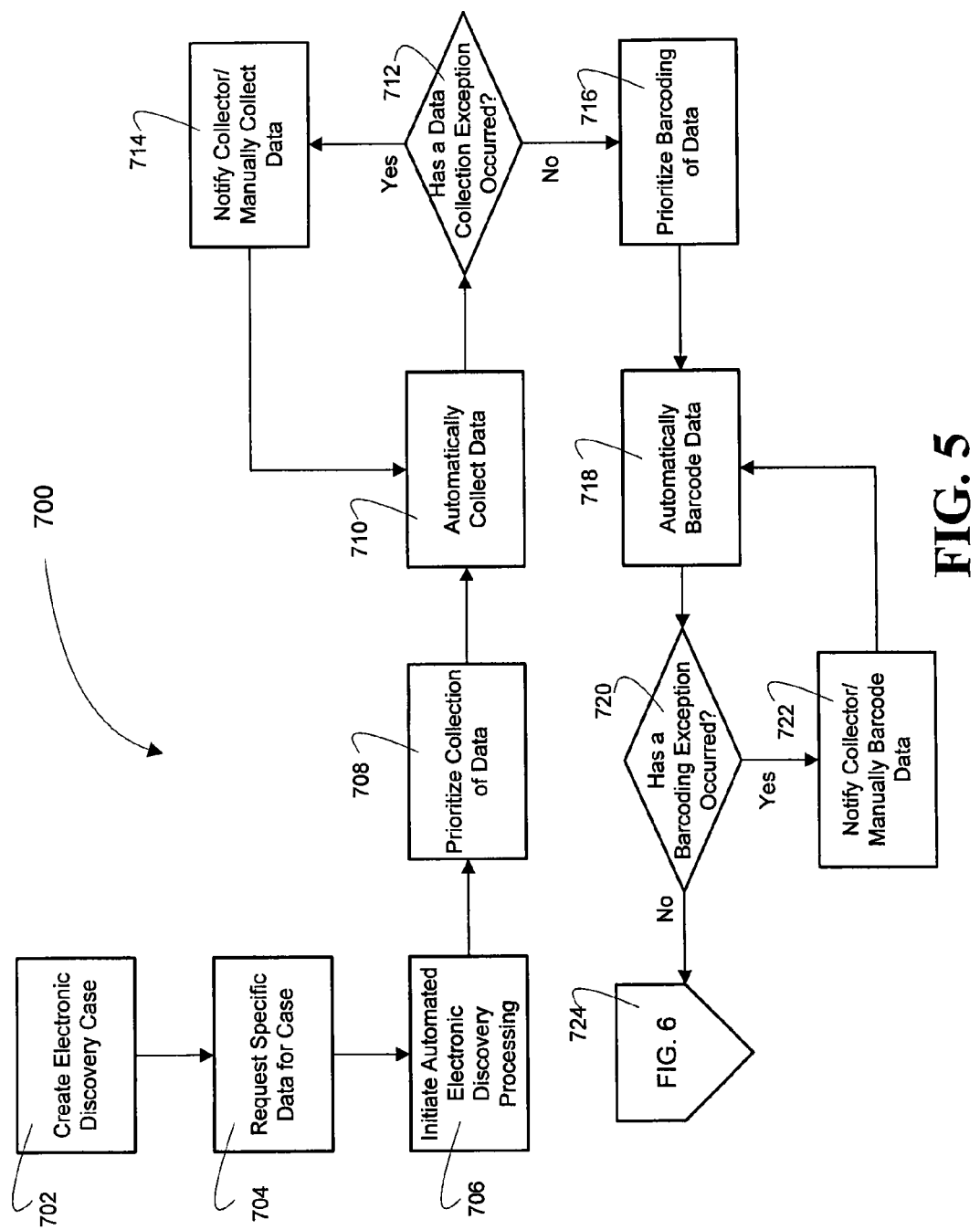
Figure 6:
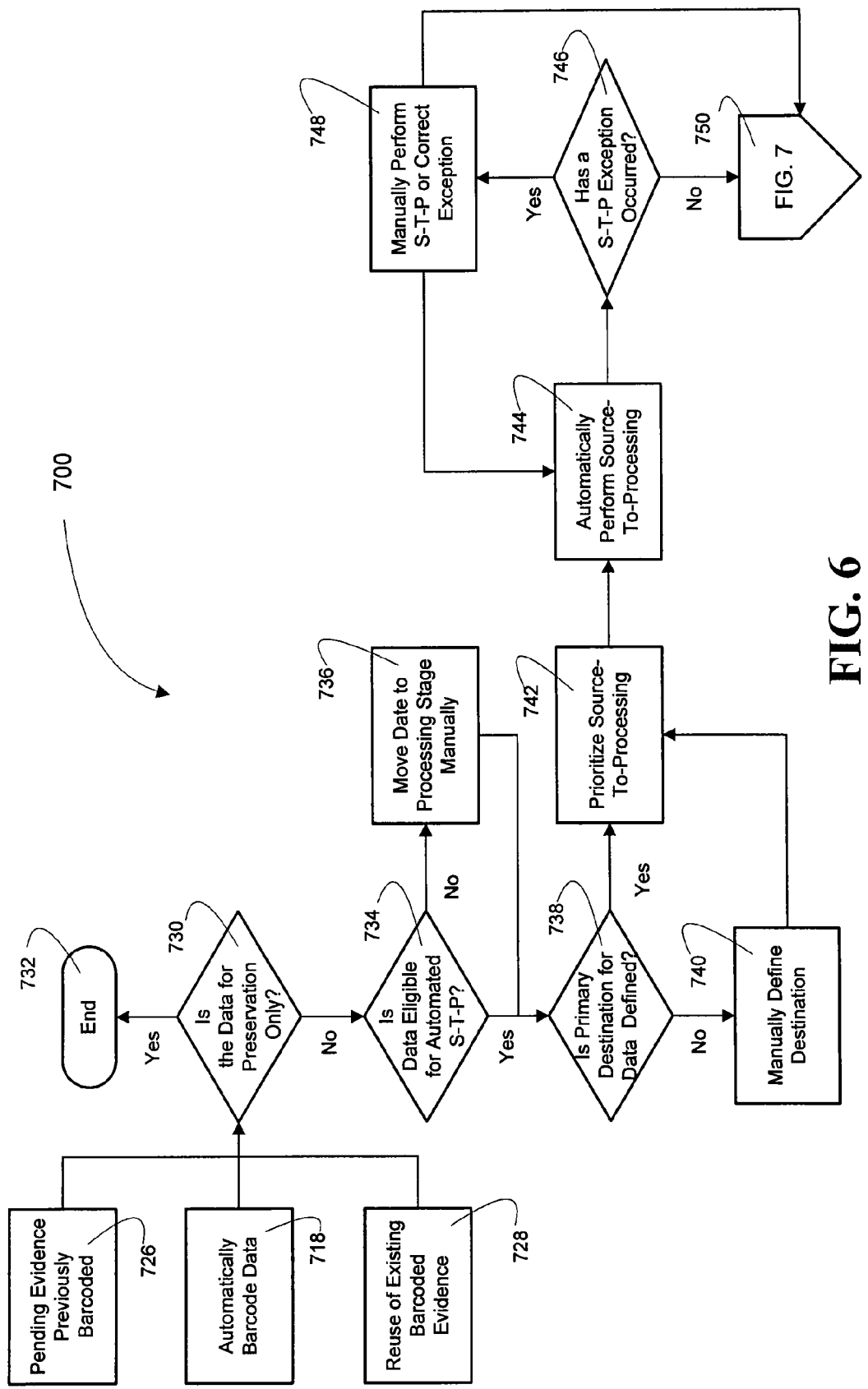
Figure 7:
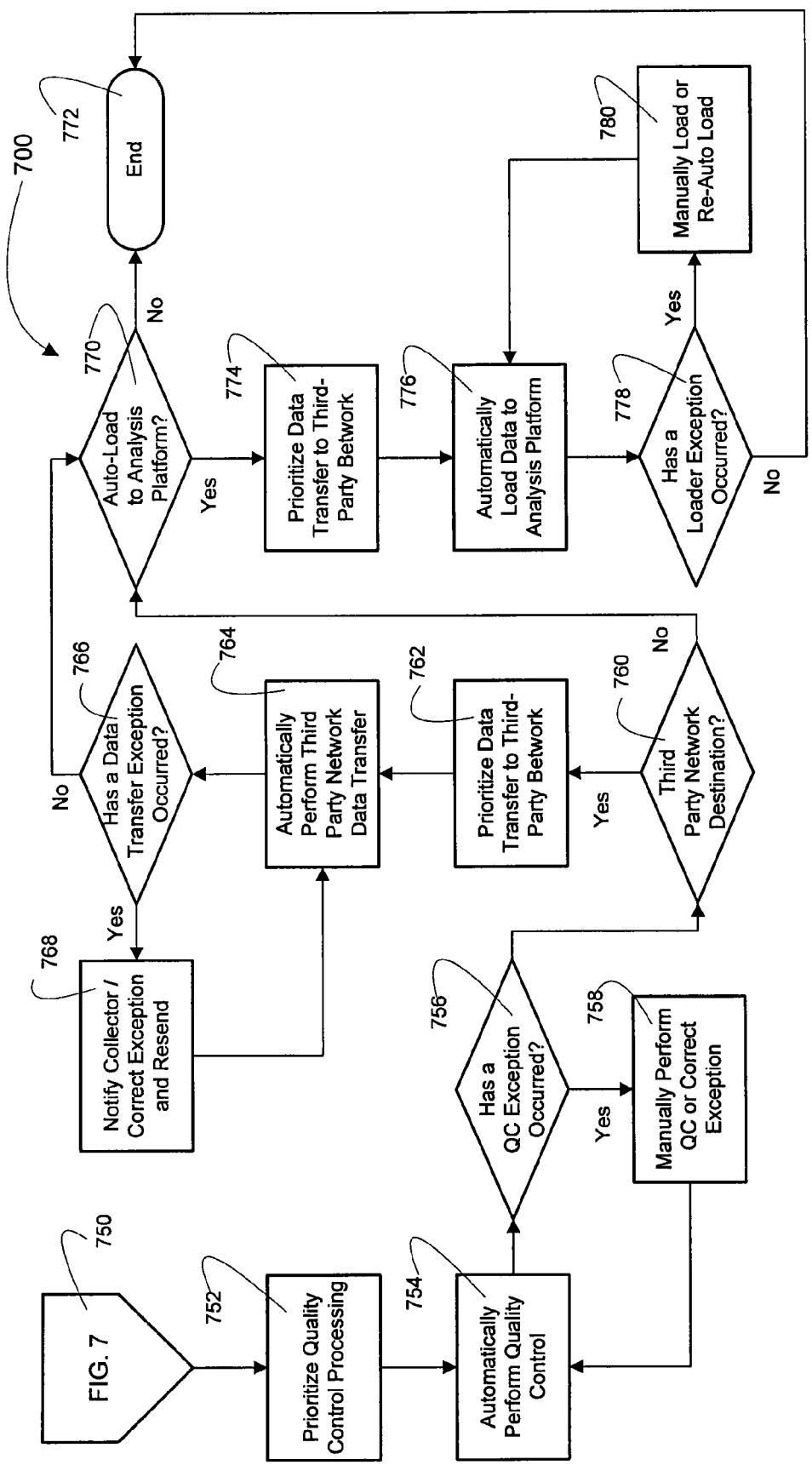
Figure 8:
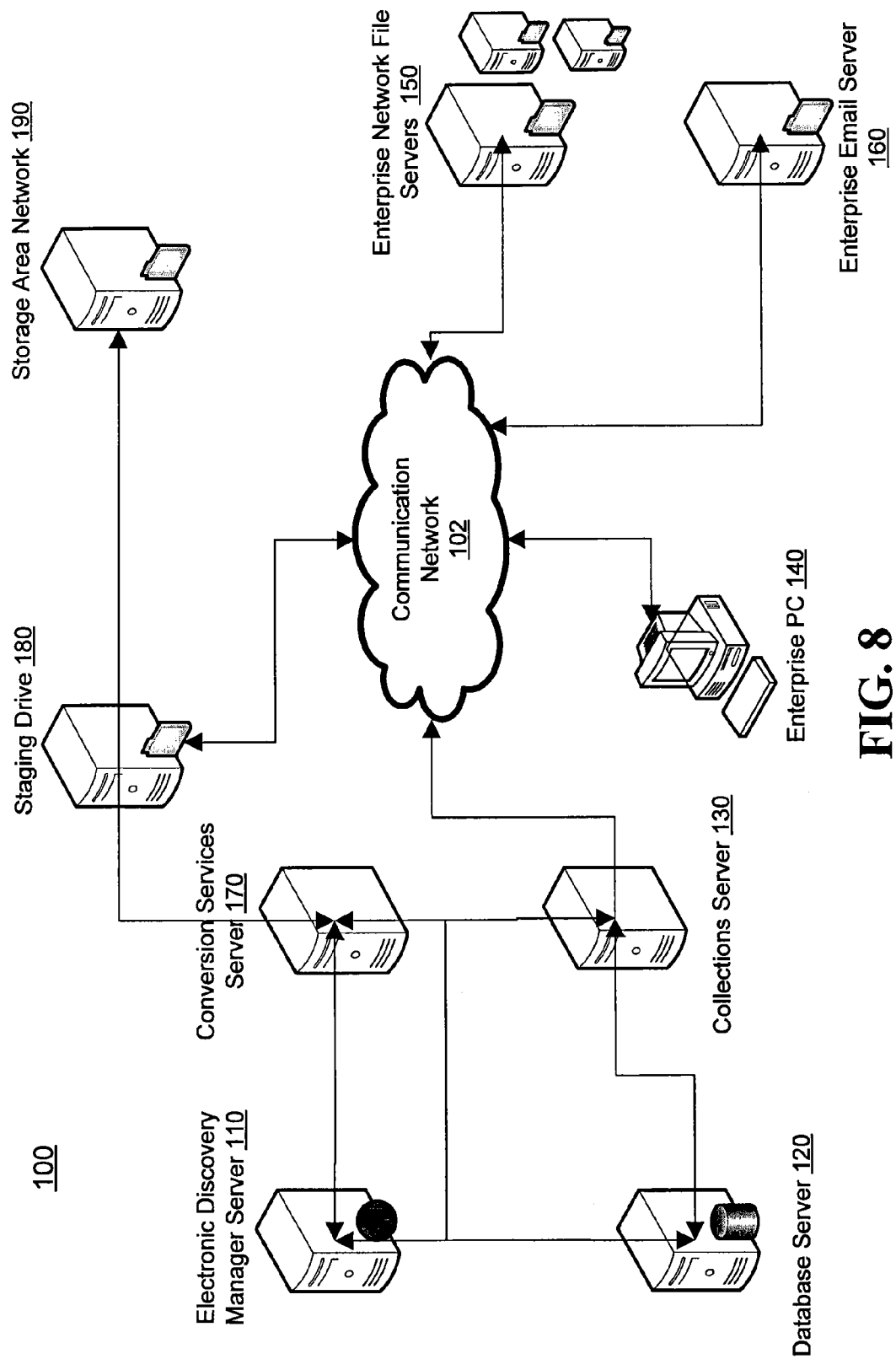
Figure 9:
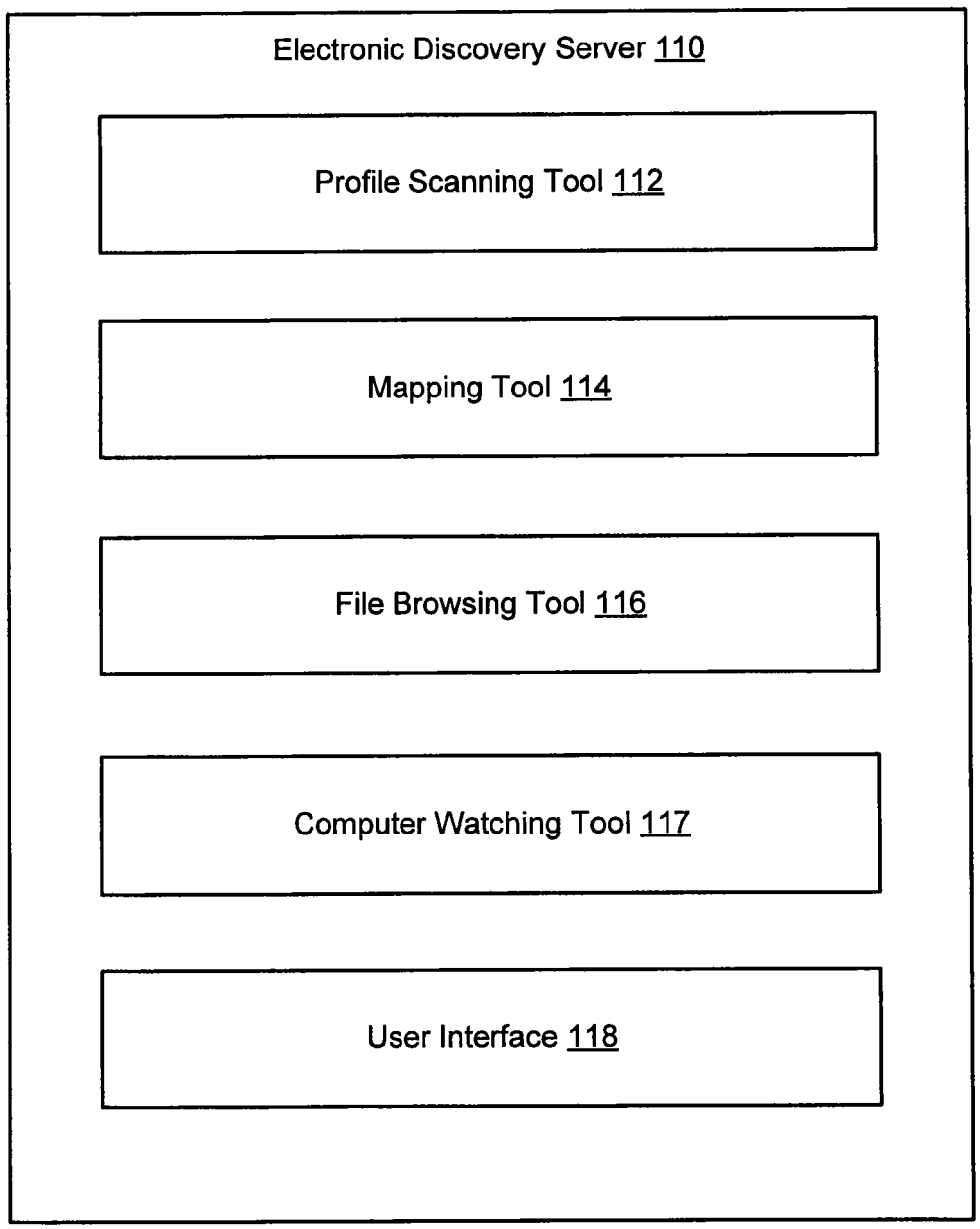
Figure 10:
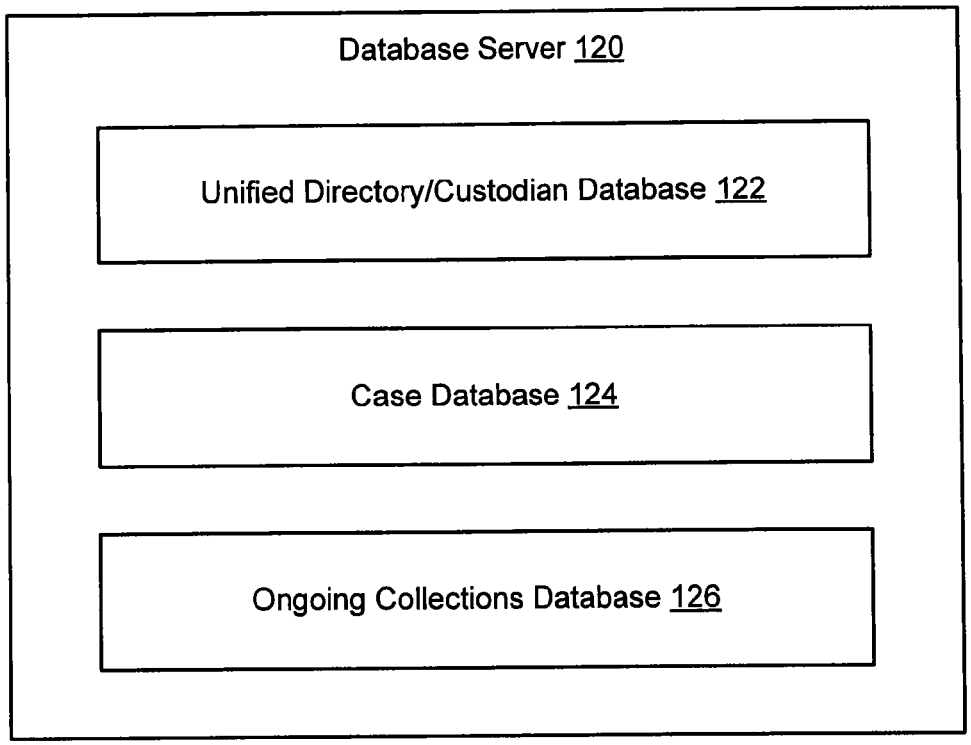
Figure 11:
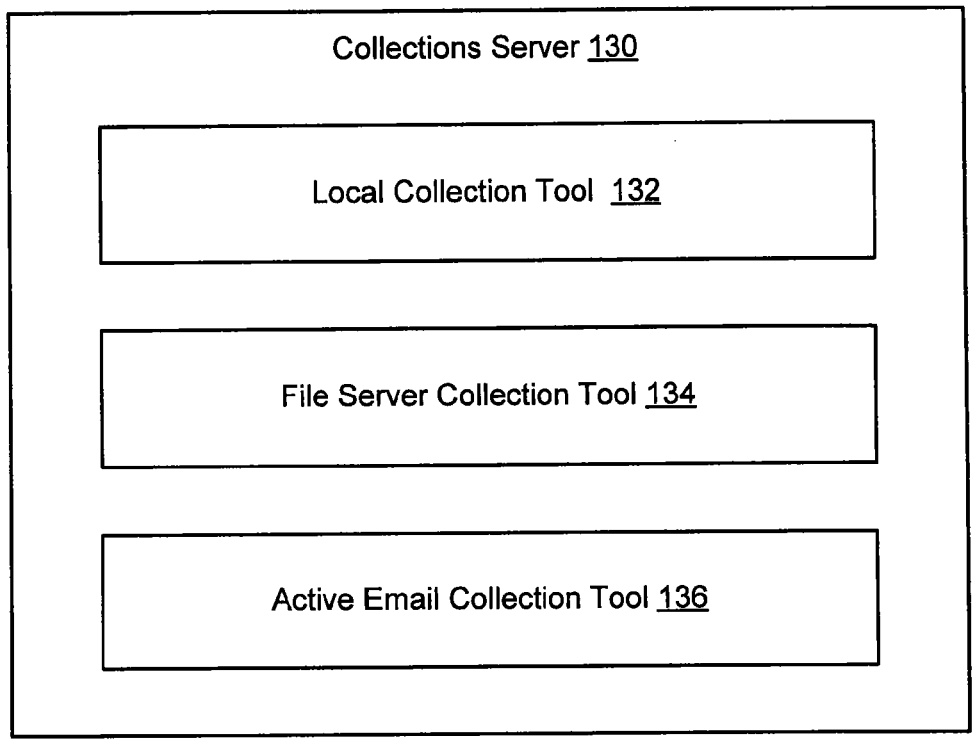
Figure 12:
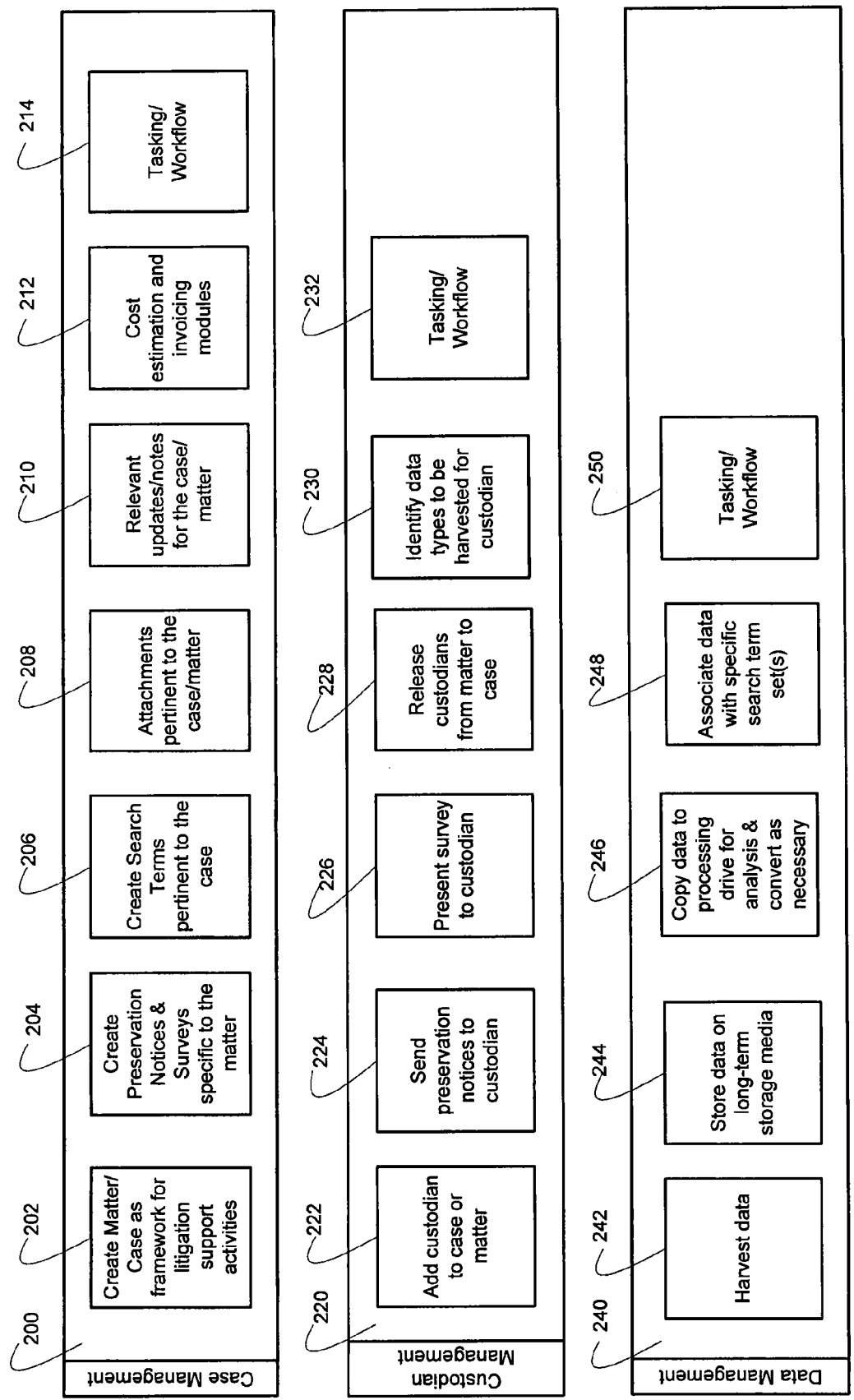
Figure 13:
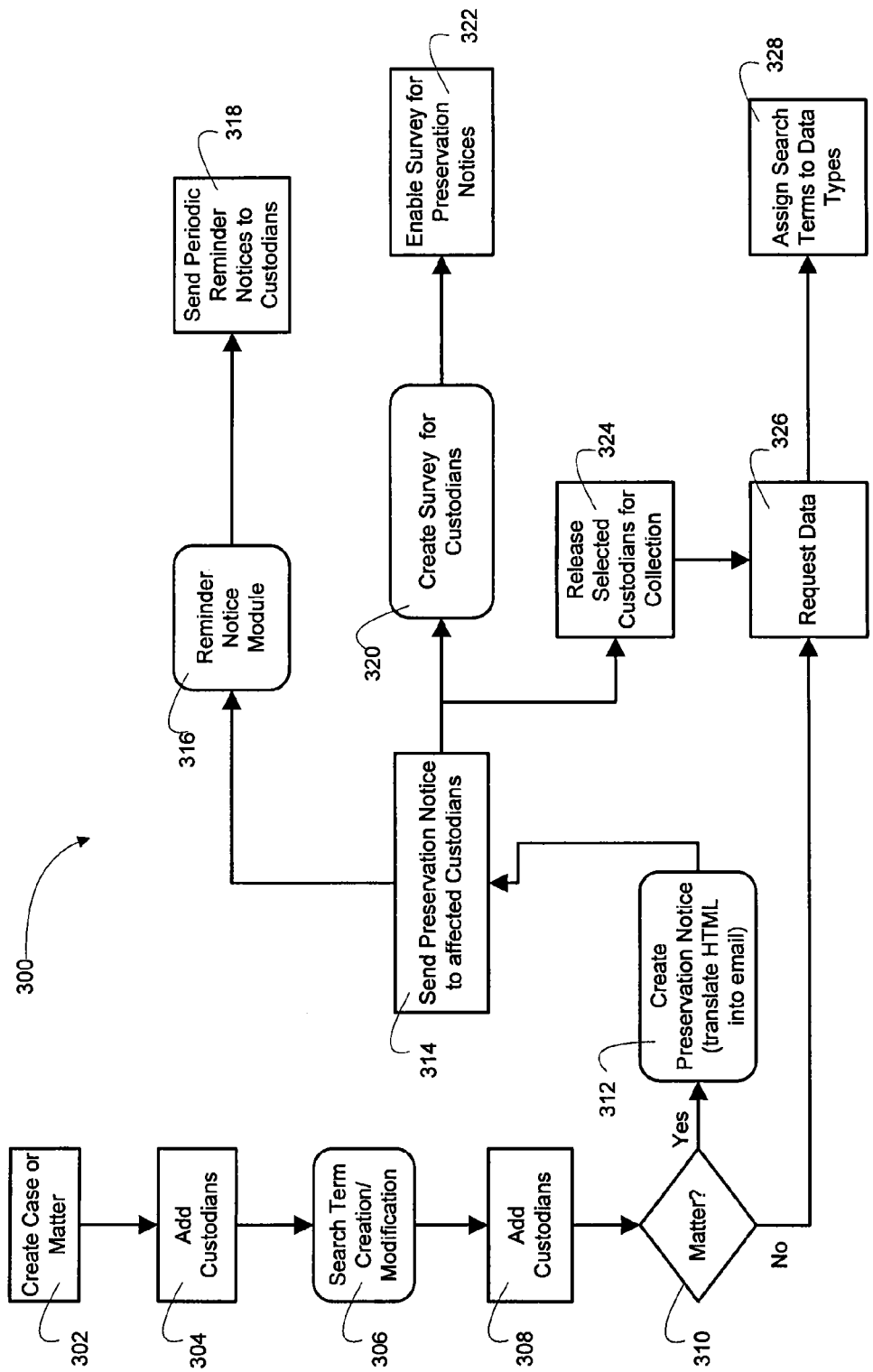
Figure 14:
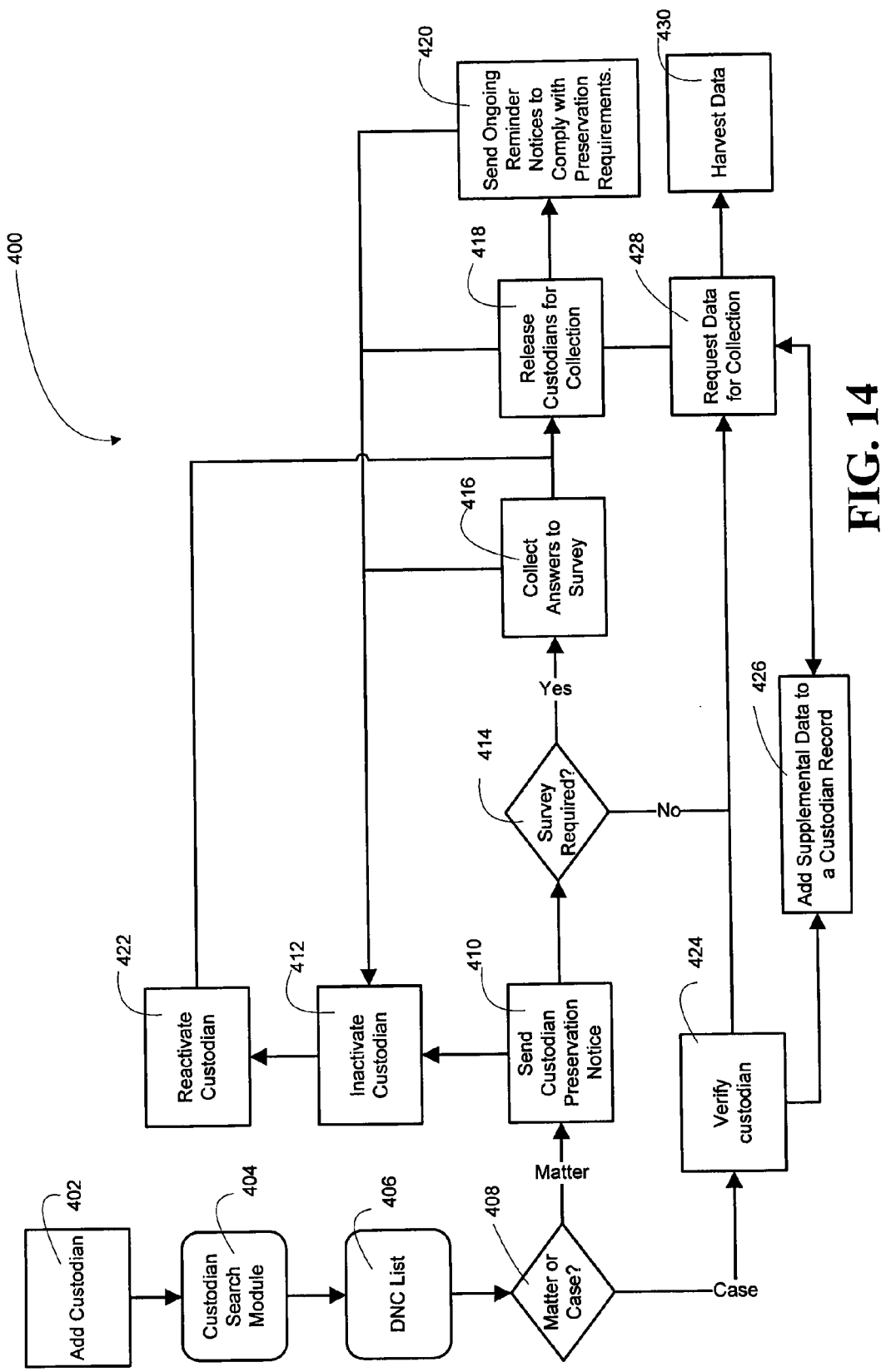
Figure 15:
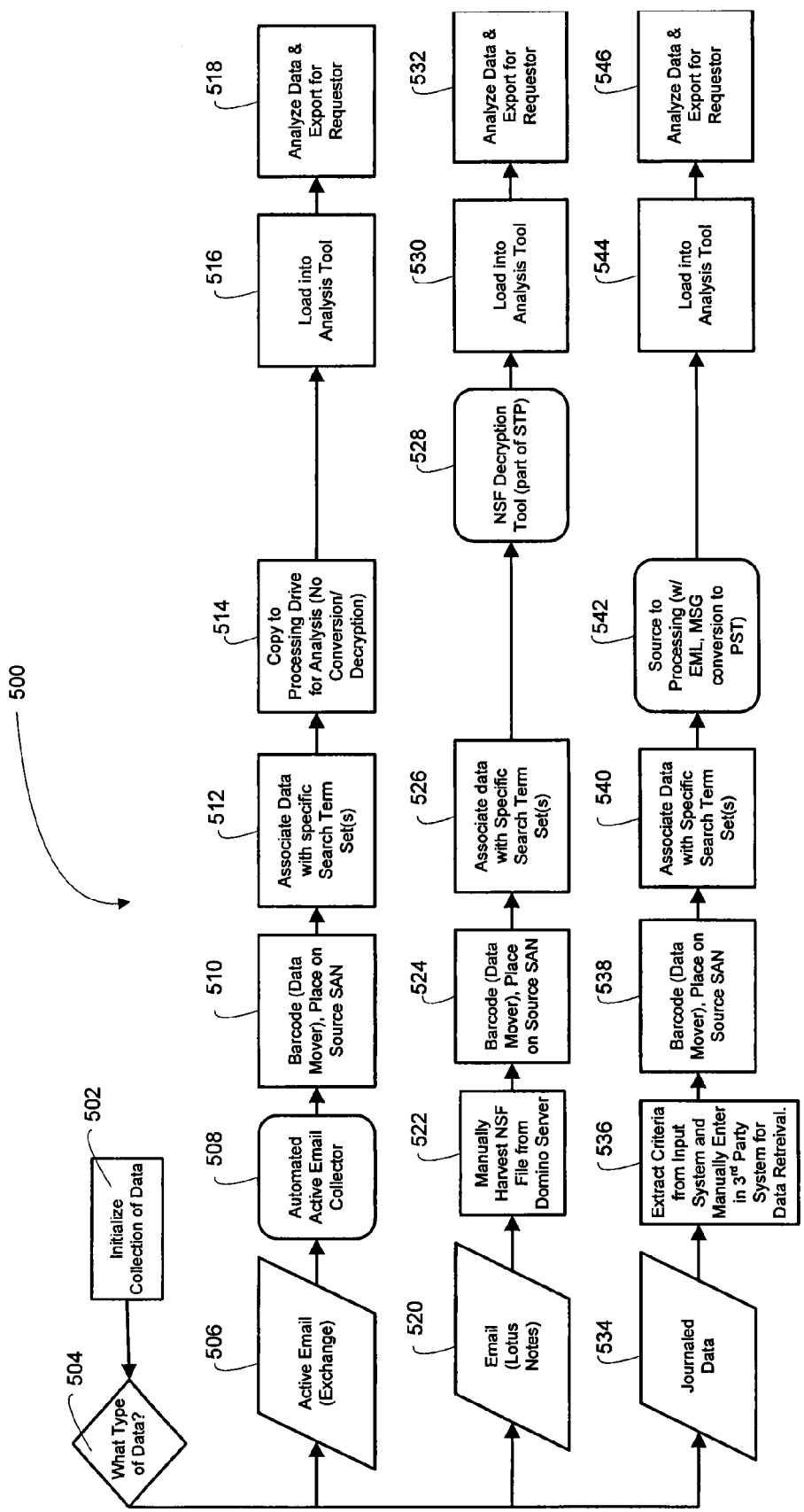
Figure 16:
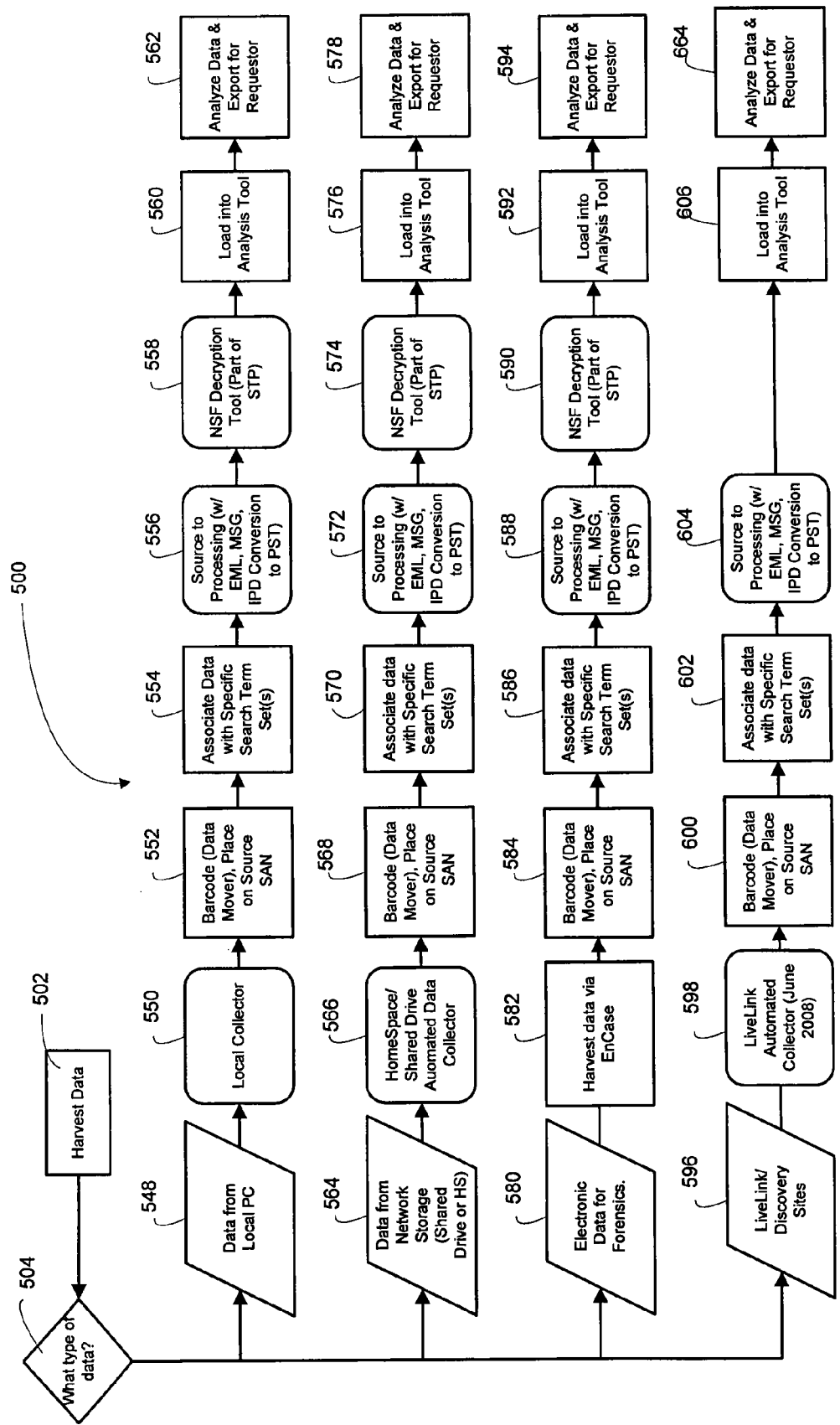

Having thus described embodiments of the invention in general terms, reference may now be made to the accompanying drawings:

FIG. 1 is a block diagram of an apparatus configured for automated straight-through processing in an electronic discovery system, according to embodiments of the present invention;

FIG. 2 is a more detailed block diagram highlighting alternate embodiments of an apparatus configured for automated straight-through processing in an electronic discovery system, in accordance with embodiments of the present invention;

FIG. 3 is a flow diagram of a method for automated straight-through processing in accordance with an embodiment of the present invention;

FIG. 4 is flow diagram of a another method for automated straight-through processing in an electronic discovery system, in accordance with embodiments of the present invention;

FIGS. 5-7 are various stages of a detailed flow diagram for automated straight-through processing in an electronic discovery system, in accordance with embodiments of the present invention;

FIG. 8 illustrates a network environment in which the processes described herein are implemented, according to one embodiment of the invention;

FIG. 9 is a block diagram of an electronic discovery manager server, in accordance with embodiment of the present invention;

FIG. 10 is a block diagram of a database server, in accordance with an embodiment of the present invention;

FIG. 11 is a block diagram of a collection server, in accordance with an embodiment of the present invention;

FIG. 12 is block diagram illustrating electronic discovery management structure, in accordance with an embodiment of the invention;

FIG. 13 is a flow diagram of a method for initiating a case or matter including creating search terms, creating and sending preservation notices, sending reminder notices and creating and sending surveys to custodians, in accordance with embodiments of the present invention;

FIG. 14 is a flow diagram of a method for custodian management in an electronic discovery system, in accordance with an embodiment of the present invention;

FIGS. 15 and 16 are flow diagrams of methods for harvesting different data types in an electronic discovery system; in accordance with an embodiment of the present invention; and FIGS. 17-21 are illustrations of exemplary user interfaces visible to a user conducting electronic discovery by means of an electronic discovery system in accordance with one embodiment of the present invention.

DETAILED DESCRIPTION OF EMBODIMENTS OF THE INVENTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

As may be appreciated by one of skill in the art, the present invention may be embodied as a method, system, computer program product, or a combination of the foregoing. Accordingly, the present invention may take the form of an entirely software embodiment (including firmware, resident software, micro-code, etc.) or an embodiment combining software and hardware aspects that may generally be referred to herein as a "system." Furthermore, embodiments of the present invention may take the form of a computer program product on a computer-readable medium having computer-usable program code embodied in the medium.

Any suitable computer-readable medium may be utilized. The computer-readable medium may be, for example but not limited to, an electronic, magnetic, optical, electromagnetic, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device; or transmission media such as those supporting the Internet or an intranet. Note that the computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of embodiments of the present invention may be written in an object oriented, scripted or unscripted programming language such as Java, Perl, Smalltalk, C++, or the like. However, the computer program code for carrying out operations of embodiments of the present invention may also be written in conventional procedural programming languages, such as the "C" programming language or similar programming languages.

Embodiments of the present invention are described below with reference to flowchart illustrations and/or block diagrams of methods, apparatus (systems), and computer program products. It may be understood that each block of the flowchart illustrations and/or block diagrams, and/or combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create mechanisms for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer readable memory produce an article of manufacture including instruction means which implement the function/act specified in the flowchart and/or block diagram block(s).

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the flowchart and/or block diagram block(s). Alternatively, computer program implemented steps or acts may be combined with operator or human implemented steps or acts in order to carry out an embodiment of the invention.

Embodiments of the present invention provide automated straight-through processing in an electronic discovery system. Further, the embodiments described herein provide for electronic discovery processes, such as, but not limited to, data collection, barcoding, source-to-processing, quality control, third-party network data transfer and data analysis platform loading to be automatically performed in pipeline fashion. Once a process is completed on a dataset, the next process in the flow is automatically initiated unless exceptions, such as, missing information or the like, which may require manual intervention, are determined to exist. In addition, embodiments provide for prioritizing cases and conducting each process in the straight-through data processing based on the case prioritization, such that, data associated with cases identified as being high-priority are performed on a next-available thread basis, while processing associated with low or no priority cases are placed in a queue and performed on a first-in, first-out basis.

Thus, present embodiments provide for an efficient means of processing data in an electronic discovery system, whereby manual intervention is minimized. As such, in general, a greater volume of data can be processed in a shorter period of time. Further present embodiments, provide for cases and related work that have been identified as having a high priority to be processed accordingly, insuring that processing related to high-priority cases is expedited through the system.

FIG. 1 is a high-level block diagram of an apparatus 10 for automated straight-through processing in an electronic discovery system. The apparatus includes a computing platform 12 having a processor and a memory 16 in communication with the processor 14. The apparatus 10 additionally includes electronic discovery processing module 18, which is stored in the memory 16 and executable by processor 14. Electronic discovery processing module 18 is configured to initiate automated straight-through processing of electronic data associated with an electronic discovery case. The automated straight-through processing of the data is initiated based on a request for the data.

The straight-through processing may include, but is not limited to, data collection, barcoding, source-to-processing functions, quality control checks, transfer of data to third-party networks, and/or loading data onto data analysis platforms. As such, straight-through processing provides for a plurality of processes to be automatically performed based on the successful completion on a preceding process. It should be noted that in specific embodiments the two or more of the processes are performed sequentially, while in other embodiments two or more of the processes may occur in parallel.

If an exception occurs during an automated process which prohibits the process from completing, remedial actions may be taken to correct or override the exception. Exceptions are defined herein as any occurrence that may prohibit the automated process from completing. Thus, exceptions include, but are not limited to, insufficient/missing information, incorrect processing; inability to perform automated processing on the data or the like. The remedial action may be an automated action or the remedial action may require notification of a case analyst/associate and manual action on behalf of the notified case analyst/associate.

Referring to FIG. 2, shown is a more detailed block diagram of apparatus 10, according to embodiments of the present invention. FIG. 2 highlights various alternate embodiments of the invention. The apparatus 10 may include one or more of any type of computerized device. The present apparatus and methods can accordingly be performed on any form of one or more computing devices.

The apparatus 10 includes computing platform 12 that can receive and execute routines and applications. Computing platform 12 includes memory 16, which may comprise volatile and non-volatile memory, such as read-only and/or random-access memory (RAM and ROM), EPROM, EEPROM, flash cards, or any memory common to computer platforms. Further, memory 16 may include one or more flash memory cells, or may be any secondary or tertiary storage device, such as magnetic media, optical media, tape, or soft or hard disk.

Further, computing platform 12 also includes processor 14, which may be an application-specific integrated circuit ("ASIC"), or other chipset, processor, logic circuit, or other data processing device. Processor 14 or other processor such as ASIC may execute an application programming interface ("API") 22 that interfaces with any resident programs, such as electronic discovery data processing module 18 and routines associated therewith or the like stored in the memory 16 of the apparatus 10.

Processor 14 may include various processing subsystems 24 embodied in hardware, firmware, software, and combinations thereof, that enable the functionality of apparatus 10 and the operability of the apparatus on a network. For example, processing subsystems 24 allow for initiating and maintaining communications and exchanging data with other networked devices. For the disclosed aspects, processing subsystems 24 of processor 14 may include any subsystem used in conjunction with electronic discovery data processing module 18 and related applications, routines, sub-routines, sub-modules thereof.

Computer platform 12 additionally may include communications module 26 embodied in hardware, firmware, software, and combinations thereof, that enables communications among the various components of the apparatus 10, as well as between the other networked devices. Thus, communication module 26 may include the requisite hardware, firmware, software and/or combinations thereof for establishing a network communication connection and transferring electronic data to a third-party network, as required.

As previously noted, the memory 16 of apparatus 10 stores electronic discovery data processing module 18, which is configured to initiate automated straight-through processing of electronic data associated with an electronic discovery case.

The electronic discovery data processing module 18 may, according to specific embodiments, include various routines for automatically processing data. While the routines are shown and described as being included within the electronic discovery data processing module 18 the routines may, according to other embodiments, be configured to be external from the electronic discovery data processing module 18.

Thus, electronic discovery data processing module 18 may include data collection routine 28 that is configured to automatically initiate data collection. As described in greater detail infra. (e.g., FIG. 10, FIG. 15 and FIG. 16) data may be collected from various sources including, but not limited to, local personal/portable computers; network storage, including shared drives; active and non-active email sources; journaled data sources; collaboration/discovery sites and the like.

Additionally, electronic discovery data processing module 18 may include barcoding routine 30 that is configured to automatically initiate barcoding of data once the data has been successfully collected. As described in greater detail infra. (e.g., FIG. 10 and FIG. 16) the barcode is generated at the time the collection process is initiated by an electronic discovery management server and acts as a folder within which all files obtained through the collection process are placed. Thus, the barcode is stored with the collected data in a long-term storage area network and is used to identify and access the data collected data at a later time. The log file of the barcode could include the time and date of the collection, the name of the requester, the particular file extension types requested, or any other information that would be useful in identifying or referring to the collection.

In other embodiments, the barcode information, or an actual link to the barcode in the long-term storage area network, is stored within a case record and/or a custodian profile at the same time that the barcode is generated. In either instance, the barcode can be used for reference by the e-discovery manager by viewing the case record or the custodian profile, as the case may be, at a later date to determine what collections have already occurred in the case or for the particular custodian. This is particularly advantageous in an enterprise environment or any environment in which multiple cases must be managed and custodians can be assigned to multiple cases, because it allows the e-discovery manager to readily locate and access data that was collected previously from a custodian, perhaps for a different case, and use the data, either for discovery purposes or to inform the collection process.

In addition, electronic discovery data processing module 18 may include source-to-processing routine 32 that is configured to automatically initiate source-to-processing functions once data has been collected and barcoded. As described in greater detail infra. (e.g., FIG. 16) source-to-processing function may include insuring that any loose files are properly formatted in a standardized format. In this regard, according to one embodiment of the invention, source-to-processing includes examining loose files for relevancy and, if relevant, storing the files in a proper data format, such as a .PST file or the like. The metadata associated with the non-standardized files is retained and remains with the reformatted data files. Source-to-processing file conversions may be required on EML formatted files, MSG formatted files, IPD formatted files and the like. Additionally, source-to-processing functions may include dividing large datasets into smaller datasets to insure efficiency at the data analysis loading process, filtering files from the dataset that do not require copying based on business rules and/or deleting invalid files from the dataset.

Electronic discovery data processing module 18 may also include quality control routine 34 that is configured to automatically initiate quality control checks once the data has completed source-to-processing. Quality control checks are administered based on predetermined rules, to insure that post source-to-processing data is valid.

Additionally, electronic discovery data processing module 18 may include third-party network data transfer routine 36 that is configured to, if required; automatically initiate transfer of the data to a predetermined third-party network based on successful completion of quality control checks. The third-party network may be any network/domain external from the enterprise network. In specific instances, the third-party network may be controlled/owned by the enterprise, such as a subsidiaries network, a co-location network or the like, while, in other instances, the third-party network may be outside of the control of the enterprise.

In addition, electronic discovery data processing module 18 may include data analysis loader routine 38 that is configured to, if required, automatically initiate loading of the data on a data analysis platform, such as, but not limited to, Attenex®, available from FTI Technology, of Seattle, Wash. As described in greater detail infra. (e.g., FIG. 16), the data analysis platform/tool provides a data reviewer the ability to analyze the data by applying search criteria or the like to the data.

The electronic discovery data processing module 18 may additionally include prioritization routine 40 that is configured to prioritize which data is processed in each process/service of the automated straight-through processing flow. According to specific embodiments prioritization may be based on case prioritization. The case prioritization criteria may include, but is not limited to, case client; age of the case; monetary risk of the case; reputational risk of the case; client-defined case categorization or the like.

In specific embodiments, the priority for each case may be determined on an ongoing basis, such as daily or the like, based on the predefined case prioritization criteria. In such embodiments, once a processing thread becomes available for each process/service in the straight-through data processing system, the data in the queue is analyzed and the data associated with the highest prioritized case is assigned to the thread and processed.

In other specific embodiments, based on predefined case prioritization criteria, specific cases may be deemed high-priority cases, requiring that data associated with such cases is prioritized. Prioritized data may require that the data be processed by a next-available processing thread as a means of expediting the processing of the data. In such embodiments, cases that are determined to be low- or no-priority cases may result in data being processed via a first-in, first-out queuing methodology.

Prioritized processing of data in accordance with automated straight-through processing assures that the system is not overloaded, minimizes the overall cycle time and provides for an increase in throughput.

Referring to FIG. 3, shown is a high-level flow diagram of a method 50 for automated straight-through processing of data in an electronic discovery system; in accordance with embodiments of the present invention. At Event 52, a computing device receives case-defining information for creating a case in an electronic discovery system. The case may be a framework for litigation support activities, forensic activities, security activities or the like. An electronic discovery associate may enter certain information about a particular case, such as a case name and/or number, a short description of the case, a legal identifier, the particular requester (i.e., who asked for the case to be opened), managers or contacts for the case (i.e., individuals involved in the substance of the case rather than the process, like the e-discovery manager) etc.

At Event 54, a computing device receives, a request for electronic data associated with the case. In specific embodiments, requesting the electronic data may be automated process, based on identification of custodians associated with a case, or, in other embodiments, a manual process, whereby an associate accesses a custodian profile, determines the data types and location to be collected.

At Event 56, automated straight-through processing of the electronic data is initiated based on the data request. As previously noted, straight-through processing of the electronic data may include, but is not limited to, data collection/harvesting; barcoding of the data; source-to-processing functions, quality control checks, transfer of data to third-party networks and/or loading of the data onto data analysis platforms.

Referring to FIG. 4, another flow diagram is presented of a method 60 for automated straight through processing of electronic data in an electronic discovery system; in accordance with embodiments of the present invention. At Event 62, an input is received, at a computing device, to create an electronic discovery case. As previously noted, an electronic discovery associate may enter certain information about a particular case, such as a case name and/or number, a short description of the case, a legal identifier, the particular requester (i.e., who asked for the case to be opened), managers or contacts for the case (i.e., individuals involved in the substance of the case rather than the process, like the e-discovery manager) etc.

At Event 64, an input is received, at a computing device that requests specific data related to the case. In specific embodiments, the requested data is associated with a custodian assigned to the case. In such embodiments, an electronic discovery associate or the like accesses a custodian profile, determines the data types and location to be collected.

At Event 66, automated straight-through processing of the electronic data is initiated by automatic prioritizing and collecting requested data in accordance with the prioritization. According to specific embodiments, prioritization is based on case prioritization. Cases may be prioritized on an ongoing basis, such as daily or the like, based on predetermined prioritization criteria, such as, but not limited to, case client, age of the case/work, monetary risk of the case, reputational risk of the case and/or client-defined case categorization. The requested data may be collected/harvested from multiple sources including, but not limited to, local personal/portable computers; network storage, including shared drives; active and non-active email sources; journaled data sources; collaboration/discovery sites and the like.

At Event 68, collected data is automatically prioritized and barcoded in accordance with the prioritization. Similar to all process/services in the automated straight-through data processing system, prioritization occurs by the same process used to prioritize the collection of data. It should be noted that the priority itself may change, if the priority listing of cases has been updated, such as, for example, if collection occurred on a first day, barcoding occurred on a second day and the prioritization was updated between the first and second days. As previously noted, barcoding acts as a folder within which all files obtained through the collection process are placed and is used to identify and access the data collected data at a later time.

At Event 70, barcoded data is automatically prioritized and source-to-processing functions are performed in accordance with the prioritization. As previously noted source-to-processing functions may include properly formatting the data in a standardized format, parsing large datasets to accommodate data analysis platforms, filtering datasets to eliminate files that do not require copying, deleting known invalid files, decrypting certain files, verifying certain types of files, copying the data to long term storage and the like.

At Event 72, automatic prioritization and quality control checks are performed in accordance with the prioritization. Quality control checks are performed in accordance with predefined business rules to ensure the validity of the post source-to-processing data.

At optional Event 74, if the data is required to be transferred to a third-party network, the data is automatically prioritized and transferred to the third-party network in accordance with the prioritization. As previously noted, data may be transferred to other networks, external from the enterprise network, such as a co-location network (otherwise referred to as a colo network).

At optional Event 76, if the data is required to be loaded onto a data analysis platform, the data is automatically prioritized and loaded onto a data analysis platform in accordance with the prioritization. The data analyst platform allows a data reviewer or the like to analyze the data by applying search terms to the dataset or the like.

FIGS. 5-7 provide a detailed flow diagram of a method 700 for automated straight-through processing of electronic data in an electronic discovery system, in accordance with embodiments of the present invention. Referring to FIG. 5, at Event 702, an electronic discovery case is created. As previously noted, the electronic discovery case may be associated with a legal matter, such as litigation; a forensic matter, a personnel matter, a security matter or the like. At Event 704 specific data is requested for a case. According to alternate embodiments, the request for data may be an automated process or a manual process. Completion of the data request triggers, at Event 706, the initiation of the straight-through data processing system of the present invention.

At Event 708, the collection of data is prioritized. Prioritization is required in the event that the resources available to collect the data are not sufficient to currently accommodate all of the requests to collect data. Thus, in the event that sufficient resources exist to accommodate all of the current data collection requests, the need to perform prioritization is obviated. As previously noted, the prioritization may be based on case priority. Case priority may be based on predefined prioritization criteria including, but not limited to, case client, age of case/work, monetary risk of case, reputational risk of case and/or client-defined case categorization.

At Event 710, based on the prioritization, the requested data is automatically collected from various sources including, but not limited to, local personal/portable computers; network storage, including shared drives; active and non-active email sources; journaled data sources; collaboration/discovery sites and the like. At Decision 712, a determination is made as to whether a data collection exception has occurred. A data collection exception is an event that results in a failure to collect all of the requested data. If the determination is made that a data collection exception has occurred, at Event 714 a data collector/analyst is notified and, based on the exception, manual collection of the data or further automated collection of the data ensues.

If the determination is made that no data collection exception has occurred or no further data collection exceptions have occurred, at Event 716, barcoding of the data is prioritized. Prioritization is required in the event that the resources available to barcode are not sufficient to currently accommodate all of the requests to barcode data. Thus, in the event that sufficient resources exist to accommodate all of the current barcoding requests, the need to perform prioritization is obviated. Prioritization of the barcoding process may occur based on the same rules used to prioritize the collection data or, in other embodiments, separate barcode prioritization rules may exist.

At Event 718, the collected data is automatically barcoded based on the determined prioritization. At Decision 720, a determination is made as to whether a barcoding exception has occurred. A barcoding exception is an event that results in a failure to barcode all of the collected data. If the determination is made that a barcode exception has occurred, at Event 722, a data collector/analyst is notified and, based on the exception, manual barcoding of the data or further automated barcoding data ensues. If the determination is made that no barcoding exception has occurred or no further barcoding exceptions have occurred, at Event 724, the flow continues to FIG. 6.

Referring to FIG. 6, in addition to data that is automatically barcoded at Event 718, other sources of electronic data may also undergo further automated straight-through processing. These other sources of data introduced into the automated straight-through processing flow include, but are not limited to, at Event 726, pending evidence previously barcoded and, at Event 728, re-use of existing evidence previously barcoded.

At Decision 730, a determination is as to whether the data is for preservation purposes only. Preservation only data is defined as data that is to be collected, identified via barcoding and stored, with no additional processing. If the determination is made that the data is for preservation only, at Event 732, further processing is deemed not necessary and the process ends. If a determination is made that the data is not for preservation only purposes, at Decision 734, a determination is made as to whether the data is eligible for automated source-to-processing copying. Eligibility may be based on the data being capable of being automatically copied to a processing drive. If the determination is made that the data is not eligible for automated source-to-processing copying, at Event 736, the data is manually moved to the processing stage.

If the determination is made that the date is eligible for automated source-to-processing, at Decision 738, a determination is made as to whether a primary processing destination for the data has been defined. If the determination is made that the primary processing destination has not been defined, at Event 740, the primary destination is manually entered by an electronic discovery associate. If the determination is made that the primary processing destination has been defined, at Event 742, source-to-processing functions are prioritized. Prioritization is required in the event that the resources available to perform source-to-processing are not sufficient to currently accommodate all of the source-to-processing requests. Thus, in the event that sufficient resources exist to accommodate all of the current source-to-processing requests, the need to perform prioritization is obviated. Prioritization of the source-to-processing process may occur based on the same rules used to prioritize the collection data and/or the barcoding of data or, in other embodiments, separate source-to-processing prioritization rules may exist.

At Event 742, source-to-processing functions are automatically performed on the data based on the determined prioritization. As previously disclosed, in addition to copying the data to a processing stage, source-to-processing functions may include, but are not limited to, formatting the data in a standardized format, parsing large datasets to accommodate data analysis platforms, filtering datasets to eliminate files that do not require copying, deleting known invalid files, decrypting certain files, verifying certain types of files, copying the data to long term storage and the like. At Decision 746, a determination is made as to whether a source-to-processing exception has occurred. A source-to-processing exception is an event that results in a failure to perform all of the required source-to-processing functions on all of the data. If the determination is made that a source-to-processing exception has occurred, at Event 748, a data analyst is notified and, based on the exception, manual source-to-processing functions are performed or further automated source-to-processing data ensues based on correction of the exception. If the determination is made that no source-to-processing exception has occurred or no further source-to-processing exceptions occurred, at Event 750, the flow continues to FIG. 7.

Turning the reader's attention to FIG. 7, at Event 752, quality control checks are prioritized. Prioritization is required in the event that the resources available to perform quality control are not sufficient to currently accommodate all of the quality control requests. Thus, in the event that sufficient resources exist to accommodate all of the current quality control requests, the need to perform prioritization is obviated. Prioritization of the quality control process may occur based on the same rules used to prioritize the collection data and/or the barcoding of data and/or source-to-processing functions or, in other embodiments, separate quality control prioritization rules may exist.

At Event 754, quality control functions are automatically performed on the data based on the determined prioritization. At Decision 756, a determination is made as to whether a quality control exception has occurred. A quality control exception is an event that results in a failure to perform all of the required quality control checks on all of the data. If the determination is made that a quality control exception has occurred, at Event 758, a data analyst is notified and, based on the exception, manual quality control checks are performed or further automated quality control checks ensue based on correction of the exception. If the determination is made that no source-to-processing exception has occurred or no further source-to-processing exceptions occurred, at Event 760, a determination is made as to whether the data requires transfer to a third-party network. As previously noted the third-party network may be any network other than the enterprise network, such as a co-location network, a subsidiary network, a network of company tangentially related to the enterprise or the like.

If the determination is made that the data requires transfer to a third-party network, at Event 762, the transfer of the data to a third-party network is prioritized. Prioritization is required in the event that the resources available to perform transfer of the data are not sufficient to currently accommodate all of the data transfer requests. Thus, in the event that sufficient resources exist to accommodate all of the current data transfer requests, the need to perform prioritization is obviated. Prioritization of the data transfer process may occur based on the same rules used to prioritize the collection data and/or the barcoding of data and/or source-to-processing functions and/or quality control checks or, in other embodiments, separate data transfer prioritization rules may exist.

At Event 764, automatic transfer of the data to a third-party network is performed based on the determined prioritization. At Decision 766, a determination is made as to whether a data transfer exception has occurred. A data transfer exception is an event that results in a failure to perform all or any portion of the data transfer. If the determination is made that a data transfer exception has occurred, at Event 768, a data analyst is notified and, based on the exception, manual data transfer is performed or further automated data transfer ensues based on correction of the exception. If the determination is made that no data transfer exception has occurred or no further data transfer exceptions occurred, or if the determination is made that no transfer of the data to a third-party network is required, at Event 770, a determination is made as to whether the data requires loading on a data analysis platform.

If the determination is made that no loading of the data onto a data analysis platform is required, at Event 772, no further processing may be required and the method ends. If a determination is made that loading of the data onto a data analysis platform is required, at Event 774, the loading of the data onto a data analysis platform is prioritized. Prioritization is required in the event that the resources available to perform loading of the data are not sufficient to currently accommodate all of the data loading requests. Thus, in the event that sufficient resources exist to accommodate all of the current data loading requests, the need to perform prioritization is obviated. Prioritization of the data loading process may occur based on the same rules used to prioritize the collection data and/or the barcoding of data and/or source-to-processing functions and/or quality control checks and/or data transfer or, in other embodiments, separate data loading prioritization rules may exist.

At Event 776, automatic loading of the data onto a data analysis platform is performed based on the determined prioritization. At Decision 778, a determination is made as to whether a data loading exception has occurred. A data loading exception is an event that results in a failure to perform all or any portion of the data loading. If the determination is made that a data loading exception has occurred, at Event 780, a data analyst is notified and, based on the exception, manual data loading is performed or further automated data loading ensues based on correction of the exception. If the determination is made that no data loading exception has occurred or no further data loading exceptions have occurred, at Event 772, the method of straight-through processing is completed and the method ends.

FIG. 8 illustrates an exemplary electronic discovery system 100 in accordance with an embodiment of the invention. In some embodiments, the environment of the electronic discovery system 100 is the information technology platform of an enterprise, for example a national or multi-national corporation, and includes a multitude of servers, machines, and network storage devices in communication with one another over a communication network. In particular, an electronic discovery management server 110, at least one database server 120, a collections server 130, enterprise personal computers 140, enterprise file servers 150, including at least one personal network storage area and at least one shared network storage area, enterprise email servers 160, a conversion services server 170, a short-term staging drive 180, and a long-term network storage network 190 are all in communication over a communication network 102. The communication network 102 may be a wide area network, including the Internet, a local area network or intranet, a wireless network, or the like.

As shown in the block diagram of FIG. 9, the electronic discovery management server 110 provides user interface management for a user via user interface 118. In some embodiments, the electronic discovery management server 110 is a web server that can be accessed via a web browser. In one particular embodiment, the electronic discovery management server 110 is an intranet website server that may be accessed utilizing a web browser on a machine within the enterprise. Through the electronic discovery management server 110, the user interface 118 may be presented to a user for the purposes of managing the electronic discovery process and all processes described herein that are inherent thereto. For illustrative purposes, it may be assumed herein that the primary user interacting with the user interface 118 is an employee or contractor of the company who serves an electronic discovery management role, and hereafter is referred to as the "e-discovery manager." As discussed in greater detail below, the e-discovery manager may utilize the user interface 118 to manage cases, custodians, collections, and collected data. It should be appreciated, however, that any individual could use the user interface 118 to perform the manual functions herein attributed to the e-discovery manager, and, indeed, that an automated process could perform those functions as well.

Referring again to FIG. 8, the electronic discovery management server 110 is in communication with the database server 120 and the collections server 130 via the communication network 102. The collection server 130 may be configured to run an application configured to manage network collection of electronic data associated with custodians residing on the network. The database server 120, as shown in the block diagram of FIG. 10, is configured to provide database services for the electronic discovery management server 110, including housing the Unified Directory/custodian database 122, which includes data relating to individual custodians, the case database 124, which includes data relating to particular cases, and ongoing collections database 126, which includes data relating to collections being undertaken by the collections server 130. Each of the foregoing databases within the database server 120 is discussed in detail below. It should be understood that multiple database servers could be employed instead of a single database server, and reference to a single database server is for illustrative and convenience purposes only. For example, the Unified Directory 122 could be stored in one database server, the case database 124 could be stored in another database server, and the ongoing collections data 126 could be stored in yet another database server.

Regardless of the number of database servers employed, it is an object of embodiments of the present invention that data relating to custodians and data relating to cases be stored in the database server 120 independently such that custodians and cases may be managed separately. While custodian data in the Unified Directory 122 and case data in the case database 124 may be linked or correlated within the database server 120, by allowing the data to be stored and managed separately in the database server 120, embodiments of the present invention advantageously foster greater efficiency in the management processes of an enterprise electronic discovery environment. For example, in an environment where custodians may be assigned to multiple cases, the effort associated with the collection of data from custodians is greatly reduced because the data relating to the custodian's storage locations does not need to be generated on a case-by-case basis or reproduced in each case record and because, in some situations, data may only be collected once from a particular custodian but used in multiple cases.

It should be understood that, as used herein, the terms "linking" and "correlating" mean associating one set or item of data stored in a first storage location with another set or item of data stored in a second storage location. For example, linking or correlating a case record to a custodian profile means associating the case data stored in a particular location with the custodian data stored in a different location. Likewise, linking or correlating a harvested data set to a case record means associating the harvested data set stored in particular location with the case data stored in a different location. The first and second storage locations may be in the same datastore or in different datastores and may be in different physical geographic locations.

When a case is initialized and a custodian is assigned to the case (because the custodian was identified as a subject for electronic discovery), information for that custodian such as network identifications, human resources information, and other data relating to data storage locations, is accessed by the electronic discovery management server 110 in the Unified Directory 122 in the database server 120 and linked to the particular case record in the case directory 124, rather than manually input by the e-discovery manager into the case. Thus, in the event the same custodian will be the subject of an electronic discovery request in multiple cases, and therefore will be assigned to multiple cases, by having the data relating to that custodian stored in a separate storage location, i.e. the Unified Directory 122, and linked to the multiple case records in the case directory 124, the e-discovery manager avoids having to re-generate and re-enter identical information about the same custodian into multiple case records.

Furthermore, in addition to allowing for management of custodians apart from cases, embodiments of the present invention also provide for management of collected data apart from cases. In this regard, in certain embodiments, the data collected from a particular custodian is stored separately from both the custodian information and any relevant case information (as discussed below, the collected data is stored in long-term storage area network 190), but is linked to a custodian, which is in turn linked to one or more cases. This is advantageous because in the event a particular custodian is assigned to multiple cases, data collected from the custodian may be shared with the other case(s) to which the custodian is assigned, which reduces the likelihood of the inefficiencies associated with over-collection. The foregoing are only two examples of the advantages brought about by the unique structure of the present invention; indeed, the separation of cases, custodians and collected data such that they may be linked together yet managed separately greatly improves the efficiency of countless processes crucial to the operation of an electronic discovery system within the environment of an enterprise or any environment with multiple custodians and multiple cases.

Thus, the various processes and components of the electronic discovery system 100 may be primarily categorized within one of case management, custodian management, or data management, although there are necessarily links between the various datastores (case, custodian, collected data) to streamline each process and ensure that each case record is complete. The particular processes and components that may be incorporated into embodiments of the present invention will now be fully explained within the context of the particular unit of work within which they primarily fall, whether it is custodian management, case management, or data management.

Custodian Management

With regard to custodian management, according to some embodiments of the present invention, the Unified Directory/custodian database 122 houses information relating to all potential custodians within the enterprise and the locations where those custodians store data. The information stored in the Unified Directory 122 may include for a particular custodian, for example, the custodian's name, position, human resources identifier (a unique number for each employee of the enterprise), employment location, domain, email addresses, network user identification, personal computer(s) name, paths of network storage devices used by the custodian, including Shared Drives and HomeSpaces, work history, related persons (such as managers, team members or subordinates), and any other information that may be relevant to the discovery process. Since the human resources identifier (perhaps a social security number) is always unique for each custodian, in some embodiments, the Unified Directory 122 may be organized around the human resources identifier. The Unified Directory 122 is generated through a multi-step process that utilizes multiple tools and methods of identifying relevant information relating to custodians and the locations in which they store data.

For example, the electronic discovery management server 110 or the database server 120 may be configured to interface with the computer databases of the human resources computer systems of the enterprise to copy the information from the human resources databases into the Unified Directory 122. In some embodiments, the electronic discovery management server 110 may also reach out to a network directory, such as Windows Active Directory, to identify network resources related to particular custodians and integrate this information into the custodian entries including the copied human resources information. Information for the Unified Directory 122 may also be obtained from the managers of the information technology network, i.e., those individuals responsible for setting up email accounts for custodians and managing the various file servers of the enterprise. Furthermore, in addition to retrieving information in the manners described above, in some embodiments, information in the Unified Directory 122 is generated through tools initialized and/or deployed by the electronic discovery management server 110. In particular, in some embodiments, as shown in FIG. 8, a profile scanning tool 112, and a mapping tool 114 are provided.

The profile scanning tool 112 may be deployed by the electronic discovery management server 110 and is configured to crawl the communication network 102, scan each of the enterprise personal computers 140, and transmit to the database server 120 identifying information about each computer, such as computer name and IP address, and a list of all profiles, including demographics information, (or network user identification) associated with each computer. According to different embodiments, the profile scanning tool 112 may be run on the electronic discovery management server 110, the collection server 130, or another server in the communication network 102. In some embodiments, the profile scanning tool 112 is further configured to identify and transmit to the database server 120 the most recent date and time at which a particular profile was logged on to the machine. According to some embodiments, when information relating to a particular computer is received by the database server 120, the database server 120 uses the profile information, which may include several user identifications, to associate the particular computer to the custodians in the Unified Directory 122 who are assigned those user identifications and store the computer names and IP addresses in those custodians' entries in the Unified Directory for future reference in collections. The database server 120 may also record in each custodian's entry in the Unified Directory 122 the last time the computer was accessed by the custodian, according to the profile information transmitted by the profile scanning tool 112. In other embodiments, the list obtained by the profile scanning tool 112 may be stored separately from the Unified Directory 122 and accessed only when a particular collection is being undertaken. Thus, the profile scanning tool 112 ultimately generates a list of personal computers used by each custodian, which list may be utilized to populate the custodian entries in the Unified Directory 122, or may be a separate directory to be utilized at the time of collection, or may be stored elsewhere, as long as it is readily accessible to the e-discovery manager when a collection of a custodian's local machine(s) is initialized, as discussed in detail below.

In accordance with some embodiments of the invention, the mapping tool 114 is configured to crawl the communication network 102 and examine the enterprise file servers 150 residing on the communication network 102 to locate and identify the path of any personal network storage area on each server. As used herein, a personal network storage area is a network storage area associated with a single user who reads data from or writes data to it. Personal network storage areas may be in the form of network storage devices or folders or other resources within a network storage device and may be referred to hereafter for clarity purposes as "HomeSpaces." According to different embodiments, the mapping tool 114 may be run on the electronic discovery management server 110, the collection server 130, or another server in the communication network 102. In some embodiments, the mapping tool 114 is a Windows service that is scheduled to execute through use of Windows Scheduled Task. As the mapping tool 114 crawls the communication network 102, it is configured to examine each file server and transmit to the database server 120 the path of any network storage area within the plurality of servers 134 that it positively identifies as a HomeSpace. In some embodiments, the mapping tool 114 is configured to explore the enterprise file servers 150 by obtaining and reviewing the directories on each server and evaluating the paths of each network storage area therein, including folders and other storage devices and resources.

With regard to identifying a particular network storage area as a HomeSpace, according to some embodiments, the mapping tool 114 is configured to utilize conventional naming techniques for paths in the communication network 102 to identify those paths of network storage areas within the enterprise file servers 150 that include an indicator, based on the conventional naming techniques, that the particular storage areas associated with those paths are accessed and used by only one user, and are therefore HomeSpaces. In accordance with some embodiments of the invention, each user of the communication network 102 is assigned to at least one user identification and those user identifications are the indicators that the mapping tool 114 attempts to locate within paths when identifying HomeSpaces. In such embodiments, it is the convention that the paths of HomeSpaces on the communication network 102 include the user's user identification. On the other hand, paths of shared network storage areas do not include user identifications. Therefore, the mapping tool 114 may explore the directories of each server within the plurality of servers, evaluate each path in turn, and make a determination as to whether or not the path includes a user identification.

If it is determined that the path includes the designated indicator, for example, a user identification, the mapping tool 114 is configured to positively identify the particular network storage area identified by that path as a HomeSpace and transmit to the database server 120 the particular user identification and the path of the HomeSpace. When that information is received by the database server 120, the database server 120 uses the user identification to link the particular HomeSpace to the custodian in the Unified Directory 122 associated with that user identification. Indeed, the HomeSpaces identified through the mapping tool 114 could be added to the relevant custodian entries in the Unified Directory 122, making them accessible to the e-Discovery manager each time those custodians are added to new cases. In other embodiments, the HomeSpace directory generated by the mapping tool 114 may be stored separately and only utilized or accessed when a particular collection is undertaken. In yet other embodiments, it could be linked to the Unified Directory 122.

In some embodiments, the mapping tool 114 is also configured to recognize and transmit, and the database server 120 is configured to house, an indication of the last time the HomeSpace was accessed by the particular user, for example, the last time any data was read from and/or written to the HomeSpace. Additionally, in some embodiments, the mapping tool 114 is configured to recognize when multiple paths map to the same network storage area. The collection server 130 compares paths for the same user to determine if duplicative entries exist. This advantageously enables avoidance of multiple collections of the same data. Thus, the profile scanning tool 112 ultimately generates a list of HomeSpaces used by each custodian, and this list may be presented to the e-discovery manager when a collection of a custodian's HomeSpaces is initialized, as discussed in detail below.

In addition to storing a list of personal computers and HomeSpaces used by a particular custodian, which lists were generated by the profile scanning tool 112 and the mapping tool 114 respectively, in accordance with some embodiments of the present invention, the database server 120 is also configured to store a list of any shared network storage areas used by the custodian. As used herein, a shared network storage area is a network storage area associated with multiple users who read data from and/or write data to it. Shared network storage areas may also be in the form of network storage devices or folders or other resources within network storage devices and may be referred to hereafter for clarity purposes as "Shared Drives." The user interface 118 is configured to receive a path of a Shared Drive input by the e-discovery manager and store the path in the Unified Directory 122 in relation to one or more custodians' human resources identifier(s). More particularly, in some embodiments, once a particular user of the communication network 102 is chosen for the collection process, the e-discovery manager may undertake to identify the particular shared network resources that that individual is using, and eventually, the paths associated with those shared network resources. This may be accomplished through conversations with the particular individual, by utilizing data returned from the local collection tool 132 executed on collection server 130 (shown in the block diagram of FIG. 11) deployed to the particular user's machine (as discussed in detail below), and/or by utilizing a file browsing tool 116 executed on electronic discovery manager server 110 (as shown in FIG. 9).

According to some embodiments of the present invention, the file browsing tool 116 is configured to be utilized by the e-discovery manager through the user interface 118. The file browsing tool 116 gives the e-discovery manager elevated authority within the communication network 102 to access, in a limited manner, the enterprise file servers 150 within the communication network 102. While the file browsing tool 116 may not allow access to the actual files stored on certain file servers, it allows the e-discovery manager to browse through the directories of the file servers 150, locate files that have been accessed by the custodian, and determine the size of the files. In accordance with some embodiments, the e-discovery manager may initially have a general idea of a particular file server within the enterprise file servers 150 that the custodian has used in the past. For example, the custodian may communicate to the e-discovery manager a particular folder name and/or drive name on which he/she has stored files. Additionally, in some embodiments, the e-discovery manager may have already undertaken a local collection process on the custodian's machine, wherein the local collection tool 132 returned a list of the network resources that the user of that machine has used. In that event, the e-discovery manager may be aware of the particular drive referenced by the user. The e-discovery manager may then employ the file browsing tool 116 to browse out to the particular drive mentioned, scan the folders for any folder having a name resembling that name given by the user, identify any particular files created by and/or accessed by the user, determine the size of such files, and retrieve the path of any folder (or Shared Drive) including data belonging to the user.

The retrieved paths of the Shared Drives may then be added, either manually or automatically, to the Unified Directory 122 in the database server 120. Thus, the Unified Directory 122 may store in connection with one custodian (and in particular in relation to the custodian's human resources identifier) a list of the personal computers, HomeSpaces, and Shared Drives associated with that custodian. Each of these locations is a potential source of data stored by the custodian, and once an investigation or collection of a custodian is initiated, the location information stored in the Unified Directory 122 may be accessed to determine the particular storage locations that need to be addressed during the investigation/collection. In other embodiments, the paths of the Shared Drives are not added to the Unified Directory 122 but merely stored in the case record 124 of one or more of the case(s) on which the custodian has been added to be accessed later when collections are initialized for the case. Therefore, according to some embodiments, the location storage information for a particular custodian is generated and stored either in the custodian's entry in the Unified Directory 122 or in another location where it is linked to the entry or otherwise readily accessible when accessing the custodian entry. Once the custodian is assigned to a particular case, the information may be automatically accessed through the Unified Directory 122 (as the custodian entry in the Unified Directory 122 is linked to the case record 124) and used to initiate collection of the custodian's files. This is advantageous and extremely efficient as it allows a completely automated investigation/collection process, rather than relying on the e-discovery manager to manually input the targeted machines and file servers at the time of collection.

It should be noted that the Unified Directory 122 may be regularly or continuously updated as new information is gathered using the tools described herein. More particularly, the electronic discovery management server 110 may be configured to automatically retrieve data from the human resources databases and Active Directory and any other relevant sources, such as information technology directories or lists, as well as deploy the profile scanning tool 112 and the mapping tool 114, at regularly scheduled intervals. Alternatively, rather than periodically retrieving data from the various data sources such as the human resources databases, the system 100 may be configured such that the database server 120 is continuously interfacing with the data sources such that the Unified Directory 122 is updated in real-time as the data within the data sources change. In either instance, each of the feeds of information into the Unified Directory 122 is regularly updated to ensure that the data in the Unified Directory 122 is current.

In some embodiments, the database server 120 is configured such that all historical data relating to a custodian is stored in relation to that custodian's human resources identifier in the Unified Directory 122. Thus, when the feeds of information into the Unified Directory 122 are updated, in the event data relating to the custodian has changed, the database server 120 is configured to store in the Unified Directory 122 the new data and any relevant metadata, including, for example, the time and date of the change, as well as maintain a record of the old data so that it is still a part of the custodian's profile in the Unified Directory 122. For example, in the event the profile scanning tool 114 identifies a new personal computer associated with a custodian and one of the personal computers associated with the custodian previously is no longer identified, the database server 120 is configured to store in the Unified Directory 122 the information for each computer, as well as indications as to when the new computer was first identified and when the old computer was no longer identified. In this way, the custodian profile within the Unified Database 122 may include a history of the personal computers used by the custodian. Such information may be relevant at the time of investigation or collection of the custodian.

One feed of information into the Unified Directory 122 which is particularly relevant to electronic discovery is employment status. According to some embodiments, when the feed of information from the human resources databases to the Unified Directory 122 includes a change as to employment status of a particular custodian, the electronic discovery management server 110 is configured to recognize the change and possibly perform particular functions in response. More specifically, in the event it is recorded in the Unified Directory 122 that the employment status of a particular custodian changes from active to terminated, the electronic discovery management server 110 is configured to determine whether the custodian is assigned to any case or matter, and, if so, to transmit to the designated manager or contact for the case or matter an electronic communication notifying the manager of the terminated status and inquiring as to whether the manager would like the terminated custodian's data collected. In the event the manager responds in the affirmative, the electronic discovery management server 110 is configured to automatically initiate the various collection processes of the present invention. Therefore, the custodian's data may be advantageously collected prior to any destruction or unavailability that could be caused by the termination. Alternatively, in other embodiments, the electronic discovery management server 110 may not communicate with the manager and may automatically initiate collection upon recognizing a change in employment status.

Case Management

With regard to case management processes, according to some embodiments, a case may be initialized by the e-discovery manager utilizing the user interface 118. In this regard, the e-discovery manager may enter into the user interface 118 certain information about a particular matter or case, such as a case name and/or number, a short description of the matter/case, a legal identifier, the particular requester (i.e., who asked for the case to be opened), managers or contacts for the matter (i.e., individuals involved in the substance of the matter rather than the process, like the e-discovery manager), custodians, etc. The electronic discovery management server 110 is configured to store this information in the case database 124 in the database server 120. The case database 124 is configured to house this information such that all information relating to a particular matter or case is related within the case database 124 and a user can use the user interface 118 to view a profile of the matter or case including all the information.

Once the matter and/or case has been initialized, the e-discovery manager may add custodians to the matter or case from whom data may be required to be collected. In some embodiments, the electronic discovery management server 110 is configured to add numerous custodians to a single matter or case at one time. In this regard, the e-discovery manager may use the user interface 118 to enter in identifying information about the custodians. The identifying information for each custodian does not have to be of the same type. For example, a name may be entered for one custodian, an email address for another, a network user identification for another, and a human resources identifier for another. The user interface 118 is configured to receive the identifying information in different input areas depending upon the type of identifying information being received. The electronic discovery management server 110 is configured to use the input information to search the Unified Directory 122 in the database server 120 to determine which custodians are associated with the input information. In the case of a human resources identifier being entered, only one custodian in the Unified Directory 122 may be a match. On the other hand, in the case of a name being entered, multiple records may be returned with explanatory details, thus enabling the e-discovery manager to select the appropriate match based on the additional details provided.

The electronic discovery management server 110, after searching the Unified Directory 122 with the input identifying information, is configured to present through the user interface 118 a list of all custodians matching the input identifying information. In the event only one match was returned for a particular set of input identifying information, the electronic discovery management server 110 is configured to automatically select the custodian to be added to the case or matter. On the other hand, in the event more than one match was located for a particular set of input identifying information, then the multiple matches may be presented together to the e-discovery manager through the user interface 118 and marked so that the e-discovery manager must review the multiple custodian profiles associated with the matches to determine the correct custodian that should be added to the case or matter. In doing so, the e-discovery manager may consider the other information in the profiles, such as corporate title, work location, associated custodians, etc. Such information can inform the e-discovery manager as to whether the located custodian is the one intended. The e-discovery manager may then select the correct custodian for addition to the case or matter and confirm that all custodians selected may be added to the case or matter.

According to some embodiments, "adding" a custodian to a case or matter involves linking the custodian profile in the Unified Directory 122 to the case or matter in the case database 124. More specifically, the electronic discovery management server 110 is configured to, once a particular custodian is identified to be added to a particular case, enter into the custodian section of the relevant case record within the case database 124 an identification of the custodian, i.e. the custodian's name, and a link to the custodian's profile in the Unified Directory. According to other embodiments, the custodian's profile information is retrieved and copied into the case record by the electronic discovery management server 110. In either instance, when a collection for a particular custodian is initiated in a particular case by the e-discovery manager, the electronic discovery management server 110 will automatically access the custodian profile for the custodian and determine the particular data storage locations that apply to that custodian. Thus, as will be discussed in detail below, in situations in which the custodian has already been added to the case and matter, the e-discovery manager must only select the particular custodian for collection, and the remaining collection process will be automated, because the Unified Directory 122 already houses all of the relevant information to access the custodian's data and the electronic discovery management server 110 is configured to automatically implement the various collection tools. This is a highly advantageous improvement over the systems of the prior art.

According to some embodiments, upon adding custodians to a matter, the electronic discovery management server 110 is configured to initiate the transmission of preservation notices and surveys to the custodians. In this regard, preservation notices and surveys relevant to the particular case or matter are stored in or linked to the case profile in the case database 124. Transmission of the preservation notices and surveys to custodians added to the case may be automated, for example, there may be preset instructions within the case profile that cause the electronic discovery management server 110 to transmit a particular preservation notice and survey at a particular date or time or upon a particular triggering event, such as a custodian being added to the case, or the e-discovery manager may manually cause the preservation notices and surveys to be transmitted. In some embodiments, the electronic discovery management server 110 is configured to transmit the preservation notices and surveys via a standard email function. The surveys may be tied to the preservation notices such that they are transmitted to custodians together, and one survey may be tied to more than one preservation notice. When a custodian responds to a survey, the survey response is received by the electronic discovery management server 110 and stored in relation to the relevant custodian in the case profile in the case database 124. In other embodiments, the architecture of the case database 124 may be configured such that it flexibly enables a user to link any/all preservation notice(s) and/or survey responses from a particular custodian to that custodian, regardless of the particular case to which the preservation notice and/or survey response relates. Furthermore, the electronic discovery management server 110 may be configured to store all or a portion of the data received in the survey response in the Unified Directory 122 in the custodian's profile.

According to some embodiments, each transmission of a preservation notice and survey to a custodian, and each corresponding response, is tracked in the relevant case profile in the case database 124. The electronic discovery management server 110 may also be configured to transmit reminder notices if responses to the surveys are not received within a predefined period of time. The electronic discovery management server 110 may also be configured to schedule reminder notices to be sent to custodians to periodically refresh the custodians' memory of their duty to preserve files/documents pertaining to the matter. In some embodiments, there is a "legal hold portal" in which the custodian is presented with a single view of all outstanding legal holds applicable to the custodian. In this legal hold portal, the custodian is presented with a comprehensive view of all outstanding notices and obligations to preserve data. If the custodian has somehow failed to acknowledge compliance with the legal hold, the legal hold portal will also provide that information to the custodian, thus providing an advantageous method of securing affirmation from the custodian. According to some embodiments, the reminder notices may be inactivated upon closure or termination of a case or matter, but can then be reactivated by the e-discovery manager. In some embodiments, once a preservation notice has been sent to a custodian, the electronic discovery management server 110 may undertake to prevent any reimaging or refreshing of the custodian's personal computer(s) by transmitting an alert of the preservation notice to the enterprise's information technology management group. In addition, the survey responses received from custodians serve to inform the collection process. For example, one survey may inquire as to what network storage devices the custodian uses when storing data. The answer that the custodian gives to the survey may inform the addition of Shared Drives to the custodian profile in the Unified Database 122 that may be used later in collection.

According to some embodiments of the present invention, the e-discovery manager may utilize the user interface 118 to add attachments, notes, tasks, and search terms to a case or matter. In some embodiments, the contacts/managers for a case may also access the case profile in the case database 124 using a web browser and may add attachments, notes, tasks, and search terms to be stored therein. Thus, the e-discovery manager may not be the only entity with access to the case and case management tools of the electronic discovery management server 110. The subject matter of the attachments, notes and tasks could be anything relevant to the case or matter. In some embodiments, the tasks are directed to the e-discovery manager or case manager or collector. In other embodiments, the tasks are tasks that particular custodians must complete and the electronic discovery management server 110 is configured to transmit a notice to the custodians that that the task needs to be completed, perhaps using standard email functions. With regard to attachments, the e-discovery manager, or the contact/manager of the case, may upload relevant files to be attached to the case profile.

With regard to the search terms, the e-discovery manager or the case contacts or managers may add certain terms to the case profile to be applied when searching the collected data to locate data responsive or relevant to the underlying issues in the case. Storing the search terms within the case profile is advantageous as it creates a record of the searching that is to be undertaken with respect to the data and aids in organization of the data, as discussed further below.

According to some embodiments of the present invention, when a decision is made that it is time to collect from certain custodians in a matter, the e-discovery manager may use the user interface 118 to release the custodians from the matter to the underlying case. This release triggers the commencement of collection of the custodians' data using the various tools of the system and the data storage information housed in the custodians' entries in the Unified Directory 122 and linked to the case record 124. Furthermore, as discussed briefly above and in detail below, from release of the custodians (i.e. selection of those custodians in the matter to be released to the case by the e-discovery manager) to collection and storage of the collected data, the process may be entirely automated. In some embodiments, the electronic discovery management server 110 is configured to allow all custodians assigned to the matter to be released to the case at the same time. In addition, in instances where the e-discovery manager has previously created groups of custodians within the case, the electronic discovery management server 110 is configured to allow a group of custodians to be released from a matter to a case at the same time. In some embodiments, automated collection of the custodian's data can occur at the time the custodian is released from the matter to the case, thus minimizing the risk of spoliation.

Data Management

Once a custodian has been identified for collection, whether manually by the e-discovery manager or by being released from a matter to a case, the electronic discovery system 100 is configured to automatically collect the custodian's data using the location information stored in the Unified Directory 122. Therefore, the electronic discovery management server 110 accesses the custodian profile of the custodian to be collected in the Unified Directory 122 and determines, from the information stored therein, the different locations of data storage for the particular custodian that must be collected. There are many different locations that the system 100 can address, including personal computers, email accounts, and network storage areas, including HomeSpaces and Shared Drives.

If a custodian profile (for a custodian released for collection) includes at least one personal computer(s) associated with the custodian, then the electronic discovery management server 110 may undertake to collect the files on these machines. Therefore, the electronic discovery management server 110 may retrieve the relevant machine identifying information, such as domain, name, IP address, etc., and may initialize deployment of a local collection tool 132 running on collections server 130 (as shown in FIG. 11).

The local collection tool 132 is configured to be deployed from the collections server 130, whether through an application running on the collections server 130 or otherwise, or another server within the network 102 to any of the enterprise personal computers 140. Therefore, for a particular custodian, the local collection tool 132 is configured to utilize the machine identifying information supplied by the electronic discovery management server 110 to be deployed to the identified custodian computer. According to one embodiment, the local collection tool 132 is configured to be automatically installed on the target custodian's personal computer. The local collection tool 132 is further configured to generate a snapshot of the data residing on the local storage of the personal computer 140, for example, by using a commercially available tool such as the Volume Shadow Copy Service, store the snapshot in a storage area on the personal computer, and transmit copies of the files included in the snapshot to the collections server 130. By transmitting the data from the snapshot of the data stored on the hard drive of the personal computer, the local collection tool 132 advantageously allows the custodian to continue to use her machine without substantial interference from the local collection tool 132 and even interact with the data stored on the hard drive as the snapshot of the data is being transmitted to the collections server 130. In some embodiments of the invention, the tool may be deployed to the users' computer and harvest all relevant files without the users' knowledge, and with no noticeable performance degradation to the users' machines. This is advantageous when attempting to collect data from a user that may be under investigation for alleged wrongdoing, for example.

In addition to the functions described above, the local collection tool 132 may also be configured to transmit to the database server 120 a catalog of the files included in the snapshot to be stored in the ongoing collections database. This catalog may be referenced by the collections server 130 in order to determine whether collection is complete and to resume interrupted collections at the point of interruption. Additionally, in accordance with some embodiments, the local collection tool 132 is configured to compile and transmit to the electronic discovery management server 110 a list of network resources the user is using, including, for example, network applications and file servers that the user has used, accessed, or mapped as network drives. This list of resources may be stored in the database server 120 in the custodian's profile in the Unified Directory 122. With regard to transmission of the files themselves, according to one embodiment of the invention, the local collection tool 132 is configured to compress, hash, and upload the files included in the snapshot to the collections server 130.

In some embodiments, the electronic discovery management server 110 may utilize a computer watching tool 117 to determine when to attempt a collection from a custodian's machine. The computer watching tool 117 is configured to monitor the network 102 and determine which of the enterprise personal computers 140 are online. Therefore, in the event there is a custodian whose local machine needs to be collected, the computer watching tool 117 is configured to determine when that machine joins the network 102 (i.e., when it appears to the computer watching tool 117) and inform the electronic discovery management server 110 that it should initialize the local collection tool 132 immediately.

If a custodian profile (for a custodian released for collection) includes any paths for HomeSpaces or Shared Drives, then the electronic discovery management server 110 may undertake to collect the files from these file servers by initializing the file server collection tool 134 running on collection server 130 (as shown in FIG. 11). The file server collection tool 134 is configured to access the file server located at the given path, whether the file server is a HomeSpace or a Shared Drive, copy the data residing on the file server, and compress, hash, and transmit the copied data to the collections server 130. The file server collection tool 134 may be programmed with preset instructions that allow it to only copy files meeting certain criteria, for example, files that have certain file extensions. Alternatively, the programmed instructions may prevent the file server collection tool 134 from copying files having certain file extensions or other attributes. Either of the foregoing is advantageous if the e-discovery manager is not interested in copying executable files or source code, for example. In some embodiments, the file server collection tool 134 is also configured to generate a size estimate of the files residing on the targeted file server. In one embodiment, the file server collection tool 134 may automatically begin the collection process (copying and transmitting data) if the size estimate falls below a predetermined threshold. In addition, in some embodiments, the file server collection tool 134 is configured to determine whether a particular folder that it is collecting from a file server includes more than a token amount of nearline files, and, in the event that the folder does include such nearline files, choose to not collect such files so as to avoid overloading the server. Therefore, according to different embodiments, the file server collection tool 134 copies all or a portion of the files residing on a file server located at the path given in the released custodian's profile and transmits them to the collections server 130.

If a custodian profile (for a custodian released for collection) includes an email address for an email account on the enterprise email server 160, then the electronic discovery management server 110 may undertake to collect the files from the enterprise email server 160 by initializing the active email collection tool 136 running on collections server 130 (as shown in FIG. 11). In some embodiments, the active email collection tool 136 is configured to access the particular Microsoft Exchange server within the enterprise email server 160 on which the custodian's account resides (which is known based on the information included in the Unified Directory 122), copy all email located there, including emails deleted by the custodian up to a predetermined period of time prior to the collection, (for example, seven days prior to the collection) and transmit the copied emails to the collections server 130.

Regardless of the storage resource location from which data is being collected, or the particular type of data being collected, the collections server 130 is configured to store the data first (while the collection is still ongoing) in the short-term staging drive 180 until the particular collection is complete, attach a barcode to the set of data resulting from the particular collection, and then copy the data set to the long-term storage area network 190 for permanent storage. In some embodiments, the barcode is generated at the time the collection process is initiated by the electronic discovery management server 110 and acts as a folder within which all files obtained through the collection process are placed. Thus, the barcode is stored with the collected data in the long-term storage area network 190 and is used to identify and access the data collected data at a later time. The log file of the barcode could include the time and date of the collection, the name of the requester, the particular file extension types requested, or any other information that would be useful in identifying or referring to the collection.

In some embodiments, the collections server 130 or another server transmits metadata about the collected data to the electronic discovery management server 110 to be stored in the database server 120, for example, in the custodian's profile in the Unified Database 122, in relation to the stored information about the particular collection, whether it was a local collection, an active email collection, a file server collection, etc. In other embodiments, the barcode information, or an actual link to the barcode in the long-term storage area network 190, is stored within the case record 124 and/or the custodian profile in the Unified Directory 122 at the same time that the barcode is generated. In either instance, the barcode can be used for reference by the e-discovery manager by viewing the case record 124 or the custodian profile, as the case may be, at a later date to determine what collections have already occurred in the case or for the particular custodian. This is particularly advantageous in an enterprise environment or any environment in which multiple cases must be managed and custodians can be assigned to multiple cases, because it allows the e-discovery manager to readily locate and access data that was collected previously from a custodian, perhaps for a different case, and use the data, either for discovery purposes or to inform the collection process.

After the data has been copied to the long-term storage area network 190, the collections server 130 compares the hashing of the data in permanent storage to the original data in the staging drive 180 and, if the hashing is identical, purges the data from the staging drive 180. Once the data has entered the long-term storage area network 190, it is not necessarily ready for review. Indeed, it is likely that the data may need to be processed before it is searchable and suitable for review by investigators and attorneys. For example, the files may be encrypted in the form in which they are collected and sent to the long-term storage area network 190. Therefore, according to some embodiments, the data may be copied to the conversion services server 170 where a series of decryption and standardization functions may be applied to it. After the data is decrypted and standardized, it is returned to the long-term storage area network 190 and may remain there to be accessed for review purposes.

With reference now to FIG. 12, a block diagram is provided that illustrates the electronic discovery management structure of the present invention, according to some embodiments. As illustrated in FIG. 12, certain processes described herein may be categorized within one of case management, as represented by Block 200, custodian management, as represented by Block 220, or data management, as represented by Block 240. As described above, the electronic discovery system 100 is arranged such that cases, custodians and data may be managed independent of one another. However, there is still an element of the categorization of processes within the categories that is conceptual, and it should be understood that certain processes may be correctly assigned to more than one category. Therefore, while the architecture of the system 100 allows separate management of custodians, cases, and data, certain processes of the present invention may affect more than one of the foregoing.

The first process that falls within the case management category is creation of a matter or case as a framework for litigation support activities, as shown in Block 202. As described above, the e-discovery manager may enter into the user interface 118 certain information about a particular matter or case, such as a case name and/or number, a short description of the matter/case, a legal identifier, the particular requester (i.e., who asked for the case to be opened), managers or contacts for the matter (i.e., individuals involved in the substance of the matter rather than the process, like the e-discovery manager) etc.

It is noted that custodian information is stored separately from the case information allowing for the same custodian in multiple cases. This provides for the electronic discovery system of the present invention to have scalability, whereby evidence associated with one custodian may be used in multiple cases.

The electronic discovery management server 110 stores this information in the case database 124 in the database server 120. The case database 124 houses this information such that all information relating to a particular matter or case is related within the case database 124 and a user, such as a manager or contact, can use the user interface 118 to view and edit a profile of the matter or case.

The next process within case management is the creation of preservation notices and surveys specific to the matter, as shown in Block 204. In this regard, the e-discovery manager may, through the user interface 118, either generate a new preservation notices or surveys relevant to the particular case or matter to be stored in the case profile in the case database 124 or, alternatively, link a preservation notice or survey already stored in the database server 120 to the case profile of the specific case or matter at issue. Also within case management is the creation of search terms pertinent to the case, as represented by Block 206. As described above, the e-discovery manager or a contact or manager for the case may use the user interface 118 to input individual search terms or search term sets to be applied to the data harvested in the case. In some embodiments, the search terms may be limited to be used with particular custodians and/or with particular harvested data types. The search terms will be saved in the case database 124 so that they may be readily applied to harvested data and used in connection with storing the resulting responsive data.

The processes of entering relevant attachments, notes and updates to a particular case or matter also falls within the case management category, as demonstrated by Blocks 208 and 210. The e-discovery manager or a case contact or manager may use the user interface 118 to upload documents and enter notes and other relevant data, including updates and reminders, to be stored in the case profile of the case in the case database 124. Once these attachments, notes and updates are added, they may be referenced whenever a user views the case profile through the user interface 118. The cost estimation modules of the present invention are also processes that are categorized as case management processes, as shown in Block 212. In this regard, the electronic discovery management server 110 utilizes a cost estimation tool to determine the cost of harvesting and reviewing data, based on a number of factors including, for example, number of custodians, amount of harvested data, data types, historical averages for specific data types, etc. Finally, case management also includes a number of tasking and workflow processes that are represented by block 214.

Moving now to custodian management, certain processes falling within the category of custodian management are shown in Block 220. While the processes involving generation of the Unified Directory 122 certainly could be categorized as custodian management, the processes shown in FIG. 12 include those processes involving management of custodians within the scope of a case or matter. In that regard, the first process of custodian management included in FIG. 12 is the addition of custodians to a case or matter, as shown in Block 222. As described above, the e-discovery manager may use the user interface 118 to link a custodian's profile from the Unified Directory 122 to the particular case profile in the case database 124. Thus, the custodian profile and case profile are correlated. The next processes within custodian management is the transmission of preservation notices and surveys to custodians, as shown in Block 224, and the presentation of the surveys to custodians, as shown in Block 226. It should be understood that, in some embodiments, the system that transmits the surveys may operate independently of the system by which the preservation notices are sent to custodians. In some embodiments, the electronic discovery management server 110 uses the contact information in the custodian's profile in the Unified Directory 122 to transmit the preservation notice(s) and survey(s) stored in the case profile to the custodian. In some embodiments, a standard email function is used, so that the only information needed from the Unified Directory 122 is the custodian's email address. When the custodian checks her email, the request to complete the survey will appear as a message therein, and when she opens that message content, the survey will be presented to her. The survey may be configured such that when she fills it out, the survey is automatically transmitted back to the database server 120 for storage in the case profile and the custodian's profile.

Also falling within custodian management is the process of releasing custodians from a matter to a case, as shown in Block 228. The e-discovery manager uses the user interface 118 to mark the custodian's profile so that the custodian is now activated for collection of data. This may occur within the case database 124 since the custodian's profile is linked thereto. Once the custodian is released, the electronic discovery management server 110 may access the custodian's profile and initialize collection based on the various data storage locations identified in the profile. Therefore, as represented by Block 230, the electronic discovery management server 110 may automatically determine the data types and locations of data to be harvested by accessing the custodian's profile in the Unified Directory 122. Alternatively, the e-discovery manager may manually make the same determination by accessing and viewing the custodian's profile. Finally, as with case management, custodian management also includes a number of tasking and workflow processes that are represented by Block 232.

The last category is data management, represented by Block 240. One major set of processes within data management are the processes relating to the harvesting of data, as shown in Block 242. These processes include the collection of data from all the different storage areas of a particular custodian, including the custodian's local storage on her personal computer(s), the custodian's network storage areas, the custodian's email, and any other areas, as are described herein. All of the data in the various storage areas is copied and transmitted to the collections server 130, as described in detail for each particular collection tool or process. Upon reaching the collections server 130, data resulting from a particular collection is temporarily stored in the short-term staging drive 180 until the collection is complete, at which point it is stored in the long-term storage area network 190 in association with a specific identifying barcode. The foregoing process is represented by Block 244. The data may require decryption or standardization functions to be applied to it in order for it to be searchable and/or otherwise usable, so the next process that falls within data management is the copying of the data to the conversion services server 170 for analysis and conversion as necessary, as shown in Block 246. Once the data is converted, it is returned to the long-term storage area network 190 to be used in review.

Also falling within data management is the association of particular data sets with particular sets of search terms stored in the case profile of the case database 124. In this regard, certain search terms stored in the case profile are stored with the intention of being applied to certain types of data, certain custodian's data, and/or a particular barcode associated with a certain collected data set. Alternatively, certain search terms may be applied to all data collected for a specific case. In either instance, the electronic discovery management server 110 accesses the case profile, determines the search terms to be applied, and associates the search terms with the barcode of the appropriate data sets in long-term storage. Thus, the search terms will be applied to that data and the results will be generated and presented to reviewers for analysis. Finally, as with the other management categories, data management also includes a number of tasking and workflow processes that are represented by Block 250.

With reference to FIG. 13, an exemplary process for managing a case is provided, in accordance with one embodiment of the present invention. As represented by Block 302, a case or matter is created by the e-discovery manager and stored in the case database 124. Next, custodians are added to the case, as shown in Block 304, by linking the custodian profiles of the Unified Directory 122 to the case profile. Next, as represented by Block 306, the e-discovery manager and/or the case contact or manager adds search terms to be applied to data harvested for the case, including instructions as to applying the search terms to particular data types or custodians. Block 310 represents the determination that must be made as to whether there is a matter or just a case. If there is no matter because preservation notices are not required, for example, for an audit, then the process will move straight to the initialization of data collection. On the other hand, if there is matter, rather than just a case, then the creation of preservation notices is required, as shown in Block 312.

The preservation notice, as shown in Block 314 is transmitted to the custodians added to the matter, perhaps using email. As shown in Block 316, a reminder notice module may be employed. As shown in Block 318, the reminder notice module transmits periodic reminder notices to custodians. The notices may be sent over email and may remind custodians about the preservation notice and/or remind custodians to fill out surveys. With regard to surveys, in the event a survey is required or desired, according to Block 320, a survey is created. The survey may be saved in the case profile in the case database 124. As shown in Block 322, it is possible to enable the survey to be attached to and transmitted with the preservation notices.

Next, as shown in Block 324, the e-discovery manager may release custodians from the matter to the case, which initialized collection of the custodian's data. As shown in Block 326, the e-discovery manager or the electronic discovery management server 122 accesses the custodian profile, determines the data types and location to be collected, and initializes the applicable collection tools to go collect the data. Once the data has been collected and a unique barcode has been assigned to each dataset based on the particular custodian and storage location from which it originated, as shown in Block 328, the search terms previously stored in the case profile may be assigned to the dataset based on the input instructions regarding the search terms. These search terms may be applied to the dataset and the results saved to be presented to reviewers for analysis.

With reference to FIG. 14, an exemplary process for managing a custodian is provided, in accordance with one embodiment of the present invention. First, as represented by Block 402, a custodian is added to a matter or case. In this regard, the custodian's profile in the Unified Directory 122 is linked to the relevant case or matter profile. In order to locate the custodian's profile, a custodian search module may be employed, as shown in Block 404. Therefore, the e-discovery manager may enter any identifying information about the custodian, whether it is the custodian's name, network user identification, email address, etc. The custodian search module will take the input information and search the Unified Directory 122 for a match. If more than one match is obtained, the user interface 118 will present all matches and allow the e-discovery manager to browse the associated profiles to determine the intended custodian. In this way, the correct custodian is identified and the profile of that custodian is linked to the appropriate case or matter.

As represented by Block 406, the electronic discovery management server 110 may determine whether the particular custodian added is a member of the enterprise "do-not-contact list." In this regard, there may be an indication in the custodian's profile in the Unified Directory 122 that the particular custodian should not be contacted regarding collections, and an alternative contact should be used, such as an administrative assistant of the custodian. Alternatively, there may be a separate do-not-contact list stored in the database server 120 that must be accessed and searched to determine whether or not the custodian appears on that list. In either instance, a determination is made as to whether or not the custodian should be directly contacted, and in the event the custodian should not be directly contacted, the contact information for the custodian's assistant (or other stand-in) should be obtained. This information will be used later for transmitting preservation notices and surveys.

Next, in accordance with Block 408, a determination is made by the electronic discovery management server 110 as to whether the custodian has been added to a matter or a case. If it is a case, then the custodian is verified, as shown in Block 424, supplemental data may be added to the custodian profile in the Unified Directory 122 as required, as shown in Block 426, and then the various collection tools are initialized by the electronic discovery management server 110 for collection of the custodian's data, as shown in Block 428. On the other hand, if it is a matter, then preservation notices may be required. Therefore, as shown in Block 410, a preservation notice is sent via email to the custodian or custodian stand-in. As shown in Block 412, the custodian may then be inactivated from the case because, for some reason, data does not need to be collected from the custodian. In the future, when it comes time to collect from the custodian, the custodian will be reactivated, as shown in Block 422. For example, a particular individual may have been added as a potential custodian, but was later deemed to be unimportant based on initial review, thus leading to inactivation. On secondary review, however, a realization may be made that this person is of importance after all, thus necessitating reactivation. Such inactivation and reactivation does not affect the actual data collection process and only impacts the matter (pre-collection) level of a particular case.

After a preservation notice is sent, a determination is made by the electronic discovery management server 110 as to whether a survey is required, as shown in Block 414. It should be noted that in alternate embodiments the decision on whether to send a survey may be made prior to sending the preservation notice. In such alternate embodiments, if the survey is required, it may become a component of the preservation notice and, thus, accessed simultaneously by the custodian. If a survey is required, it is transmitted in conjunction with a preservation notice, and the answers are collected by the electronic discovery management server 110 and stored in the database server 120, as shown in Block 416. Reminder notices for the preservation notices and surveys may also be transmitted to the custodian, as shown in Block 420. Next, once it is time to collect data, the custodian is released from the matter to the case, as shown in Block 418, and the various collection tools are initialized by the electronic discovery management server 110 for collection of the custodian's data, as shown in Block 428. In this process, the custodian's profile in the Unified Directory 122 is accessed in order to determine the various locations where the custodian may have stored data. Finally, as shown in Block 430, the custodian's data is collected.

Referring to FIGS. 15 and 16, flow diagrams are presented of a method 500 for harvest data from various data sources, in accordance with embodiments of the present invention. At Event 502, the process whereby data is collected is initiated and, at Event 504, the type of data is identified. Data Block 506 signifies active email that is collected from an exchange system or the like. At Event 508 the automated active email collection tool is implemented to collect email from identified email address. As previously noted, and in accordance with present embodiments of the invention, if a custodian profile (for a custodian released for collection) includes an email address for an email account on the enterprise email server (160), then the electronic discovery management server (110) may undertake to collect the files from the enterprise email server (160) by initializing the active email collection tool (136) running on collections server (130). In some embodiments, the active email collection tool (136) is configured to access the particular Microsoft Exchange server within the enterprise email server 160 on which the custodian's account resides (which is known based on the information included in the Unified Directory 122), copy all email located there, including emails deleted up to a designated prior period, for example, seven days prior to the collection, and transmit the copied emails to the collections server (130). The email collection tool is also capable of implementing bulk requests and for collecting email on a scheduled basis, such as daily. The email collection tool is additionally capable of being implementing enterprise wide and requires no server identifiers or the like to collect the active email. In this regard, the email collection tool (136) serves to reduce security risk.

At Event 510, a barcoding tool is implemented at a staging location, such as short-term staging drive (180) to attach a barcode to the set of email resulting from the particular collection. The barcoded data is then copied and communicated to the long-term storage area network (190) for permanent storage. Furthermore, the collections server (130) transmits the barcode information to the electronic discovery management server (110) to be stored in the database server (120), for example, in the custodian's profile in the Unified Database (122), in relation to the stored information about the particular collection. Therefore, the barcode can be used for reference at a later date to determine the origin of the data. After the data has been copied to the long-term storage area network (190), the collections server (130) compares the hashing of the data in permanent storage to the original data in the staging drive (180) and, if the hashing is identical, purges the data from the staging drive (180). As such, barcoding is performed without the need to execute the barcoding tool on an exchange server and, as such no human intervention is needed in the barcode process. In accordance with embodiments of the present invention, one barcode may be assigned per custodian, per data type and per event (i.e., case, matter, etc.)

At Event 512, the collected email data may be associated with a specific search term set or sets. When the search terms are applied, a listing of the files and documents including those terms (the "search term hit list") are presented to the reviewer and also stored in the database server (120). The reviewer may provide an indication of this to the electronic discovery management server 110, which may then make a determination that other documents within the search term hit list are more likely to be responsive.

At Event 514, the collected and barcoded active email data is copied to a processing drive for subsequent analysis. It should be noted that the nature of email data obviates the need to perform conversion and/or decryption on the data set. At Event 516, the active email data set is loaded into the analysis tool and, at Event 518, the data set is exported to the requestor/reviewer for analysis.

Data Block 520 signifies other non-exchange server based email, such as email accessed through a client-server, collaborative application, such as Lotus Notes® or the like. At Event 522, NSF files or any other file types associated with non-exchange server based email is manually harvested from an enterprise-grade email server having collaborative capabilities, such as a Lotus Domino server or the like.

At Event 522, a barcoding tool is implemented at a staging location, such as short-term staging drive (180) to attach a barcode to the set of non-exchange server email resulting from the particular collection. The barcoded data is then copied and communicated to the long-term storage area network (190) for permanent storage. Furthermore, the collections server (130) transmits the barcode information to the electronic discovery management server (110) to be stored in the database server (120), for example, in the custodian's profile in the Unified Database (122), in relation to the stored information about the particular collection. Therefore, the barcode can be used for reference at a later date to determine the origin of the data. After the data has been copied to the long-term storage area network (190), the collections server (130) compares the hashing of the data in permanent storage to the original data in the staging drive (180) and, if the hashing is identical, purges the data from the staging drive (180).

At Event 526, the collected non-exchange server email data may be associated with a specific search term set or sets. When the search terms are applied, a listing of the files and documents including those terms (the "search term hit list") are presented to the reviewer and also stored in the database server (120). The reviewer may provide an indication of this to the electronic discovery management server 110, which may then make a determination that other documents within the search term hit list are more likely to be responsive.

At Event 528, the NSF files or any other file types associated with non-exchange server based email that may be encrypted is decrypted using a decryption tool, in accordance with embodiments of the present invention. The encryption of NSF files occurs at the user level and, therefore only the user has the password necessary for decryption. The decryption tool allows for decryption of the NSF file-type data without the knowledge of the user/encrypter. The decryption tool finds ID files that exist anywhere in the enterprise system, creates a database of the ID files, associates the database with the user/encrypter and subsequently decrypts the data.

At Event 530, the non-exchange server email data set is loaded into the analysis tool and, at Event 532, the data set is exported to the requestor/reviewer for analysis.

Data Block 534 signifies journaled data, such as electronic commerce data stored on a repository for the purpose of regulation, compliance to regulating bodies, such as the Securities and Exchange Commission (SEC) or the like. At Event 536, criteria is extracted from input system and manually entered in a designated third-party system for data retrieval.

At Event 538, the barcoding tool is implemented at a staging location, such as short-term staging drive (180) to attach a barcode to the set of journaled data resulting from the particular collection. The barcoded data is then copied and communicated to the long-term storage area network (190) for permanent storage. At Event 540, the collected and barcoded journaled data may be associated with a specific search term set or sets.

At Event 542 source-to-processing is implemented to insure that any loose files are properly formatted in a standardized format. In this regard, according to one embodiment of the invention, loose files are examined for relevancy and, if relevant, stored in a proper data format, such as a PST file or the like. The metadata associated with the non-standardized files is retained and remains with the reformatted data files. Source-to-processing file conversions may be required on EML formatted files, MSG formatted files and the like.

At Event 544, the journaled data set is loaded into the analysis tool and, at Event 546, the journaled data set is exported to the requestor/reviewer for analysis.

Referring to FIG. 16, data block 548 signifies data from a local Personal Computer (PC), such as enterprise PC (140). At Event 550, the local collection tool (132) is implemented to collect data from designated PCs by taking a "snapshot" of the device's hard drive. According to one embodiment of the invention, the local collection tool may be autodeployed thus, obviating the need for any manual entry by the e-discovery manager or the like. In other embodiments of the invention, the local collection tool (132) may be employed to collect data from network storage.

At Event 552, the barcoding tool is implemented at a staging location, such as short-term staging drive (180) to attach a barcode to the set of local PC data resulting from the particular collection. The barcoded data is then copied and communicated to the long-term storage area network (190) for permanent storage. At Event 554, the collected and barcoded local PC data may be associated with a specific search term set or sets.

At Event 556 source-to-processing is implemented to insure that any loose files are properly formatted in a standardized format. In this regard, according to one embodiment of the invention, loose files are examined for relevancy and, if relevant, stored in a proper data format, such as a PST file or the like. The metadata associated with the non-standardized files is retained and remains with the reformatted data files. Source-to-processing file conversions may be required on EML formatted files, MSG formatted files, IPD formatted files and the like.

At Event 558, the local PC files that may be encrypted are decrypted using a decryption tool, in accordance with embodiments of the present invention. The decryption tool allows for decryption of the PC files data without the knowledge of the user/encrypter. The decryption tool finds ID files that exist anywhere in the enterprise system, creates a database of the ID files, associates the database with the user/encrypter and subsequently decrypts the data.

At Event 560, the local PC data set is loaded into the analysis tool and, at Event 562, the local PC data set is exported to the requestor/reviewer for analysis.

Data block 564 signifies data from network storage, such as a shared drive or HomeSpace. At Event 566, the file server collection tool (134) is implemented to automatically collect data from shared drives and/or HomeSpace. According to one embodiment of the invention, the file server collection tool (134) may be autodeployed thus, obviating the need for any manual entry by the e-discovery manager or the like.

At Event 568, the barcoding tool is implemented at a staging location, such as short-term staging drive (180) to attach a barcode to the set of network storage data resulting from the particular collection. The barcoded data is then copied and communicated to the long-term storage area network (190) for permanent storage. At Event 570, the collected and barcoded network storage data may be associated with a specific search term set or sets.

At Event 572 source-to-processing is implemented to insure that any loose files are properly formatted in a standardized format. In this regard, according to one embodiment of the invention, loose files are examined for relevancy and, if relevant, stored in a proper data format, such as a PST file or the like. The metadata associated with the non-standardized files is retained and remains with the reformatted data files. Source-to-processing file conversions may be required on EML formatted files, MSG formatted files, IPD formatted files and the like.

At Event 574, the network storage files that may be encrypted are decrypted using a decryption tool, in accordance with embodiments of the present invention. The decryption tool allows for decryption of the network storage data without the knowledge of the user/encrypter. The decryption tool finds ID files that exist anywhere in the enterprise system, creates a database of the ID files, associates the database with the user/encrypter and subsequently decrypts the data.

At Event 576, the network storage data set is loaded into the analysis tool and, at Event 578, the network storage data set is exported to the requestor/reviewer for analysis.

Data block 580 signifies electronic data for forensics. At Event 582, a forensic collector tool, such as EnCase® may be executed on the devices of interest to collect data. According to one embodiment of the invention, the forensic collector tool may be automatically deployed on the device of interest without the knowledge of the device user. In accordance with another embodiment of the invention, a computer watcher tool may be implemented (not shown in FIG. 16) that watches the network to determine the addition or subtraction of computers to the network based on ID's/IP addresses returned from the network.

At Event 584, the barcoding tool is implemented at a staging location, such as short-term staging drive (180) to attach a barcode to the set of forensic data resulting from the particular collection. The barcoded data is then copied and communicated to the long-term storage area network (190) for permanent storage. At Event 586, the collected and barcoded forensic data may be associated with a specific search term set or sets.

At Event 588 source-to-processing is implemented to insure that any loose files are properly formatted in a standardized format. In this regard, according to one embodiment of the invention, loose files are examined for relevancy and, if relevant, stored in a proper data format, such as a PST file or the like. The metadata associated with the non-standardized files is retained and remains with the reformatted data files. Source-to-processing may be required on EML formatted files, MSG formatted files, IPD formatted files and the like.

At Event 590, the forensic files that may be encrypted are decrypted using a decryption tool, in accordance with embodiments of the present invention. The decryption tool allows for decryption of the network storage data without the knowledge of the user/encrypter. The decryption tool finds ID files that exist anywhere in the enterprise system, creates a database of the ID files, associates the database with the user/encrypter and subsequently decrypts the data.

At Event 592, the forensic data set is loaded into the analysis tool and, at Event 594, the network storage data set is exported to the requestor/reviewer for analysis.

Data block 596 signifies collaborative data, such as data residing at discovery sites, for example LiveLink® or the like. At Event 598, a discovery site collector tool, such as a LiveLink® collector tool may be executed on the devices of interest to collect data. According to one embodiment of the invention, the discovery site collector preserves at least a portion of the discovery site database in the e-discovery database, including all files and all revisions of the files. In this regard, the discovery site collector tool queries against the database to define what files need to be retrieved, then copies those files based on the result of the query. Metadata pertaining to the files is retained in the case management system tables. In accordance with another embodiment of the invention, the discovery site collector tool collects the documents and the related metadata and uses the metadata to automatically rename the files.

At Event 600, the barcoding tool is implemented at a staging location, such as short-term staging drive (180) to attach a barcode to the set of discovery site data resulting from the particular collection. The barcoded data is then copied and communicated to the long-term storage area network (190) for permanent storage. At Event 602, the collected and barcoded discovery site data may be associated with a specific search term set or sets.

At Event 604 source-to-processing is implemented to insure that any loose files are properly formatted in a standardized format. In this regard, according to one embodiment of the invention, loose files are examined for relevancy and, if relevant, stored in a proper data format, such as a PST file or the like. The metadata associated with the non-standardized files is retained and remains with the reformatted data files. Source-to-processing may be required on EML formatted files, MSG formatted files, IPD formatted files and the like.

At Event 606, the discovery site data set is loaded into the analysis tool and, at Event 608, the discovery site data set is exported to the requestor/reviewer for analysis.

Figure 17:
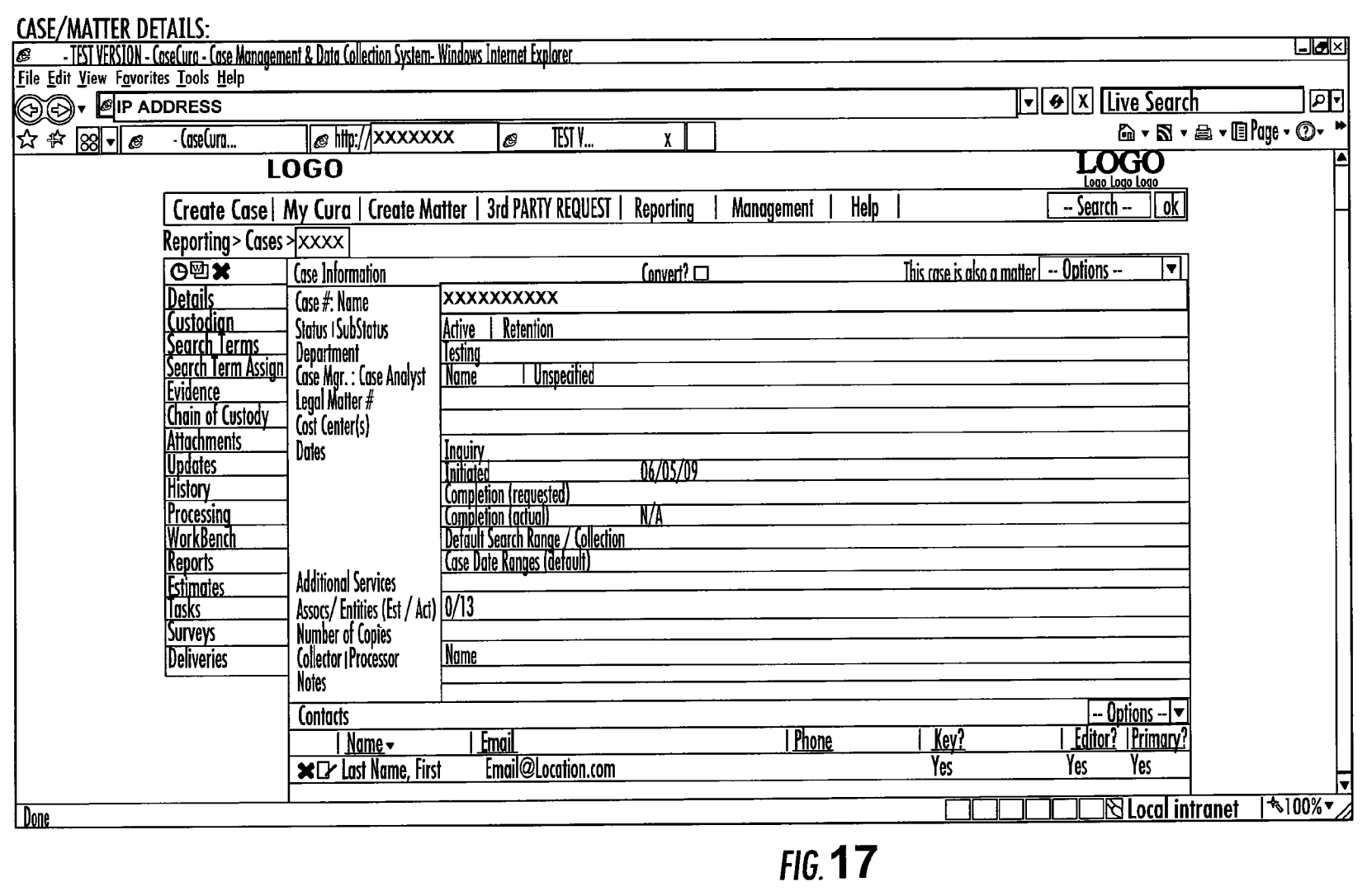

In order to illustrate the efficiencies and advantages provided by the unique structure of embodiments of the present invention, that is, separating the storage and management of custodians, cases, and collected data but allowing linkages between them, FIGS. 17-21 provide illustrations of the user interface 118 visible to the e-discovery manager conducting electronic discovery using an exemplary electronic discovery system in accordance with one embodiment of the present invention. Referring to FIG. 17, a screen shot of an exemplary case record within the case database 124 is provided. The most general case information appears on the main page, with options on the left-hand side given to link to other information about the case on different pages, most notably, custodians and evidence (collected data). As discussed previously, both the custodian profiles and the collected data are not housed exclusively in the case record, but rather are stored elsewhere (the Unified Directory 122 and the long-term storage area network 190 respectively) and linked to the case record to promote efficiency within an enterprise electronic discovery environment.

Figure 18:
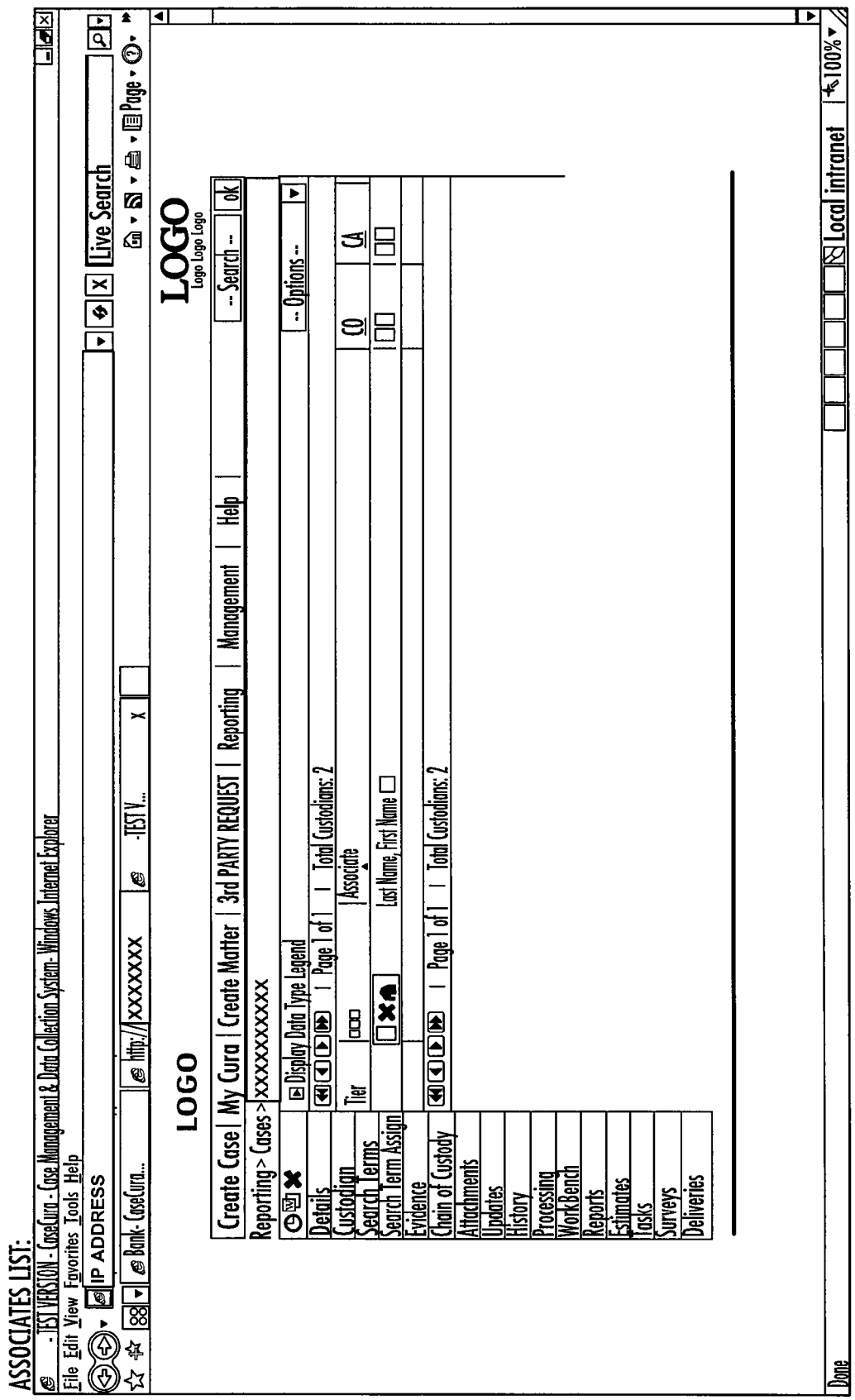

Referring to FIG. 18, a screen shot of the custodian page of the case record is provided. The custodian list shown is housed within the case record in the case database 124, but each custodian name is a hyperlink to the custodian profile within the Unified Directory 122. In some embodiments where the custodian profile in the Unified Directory 122 does not contain all information about the custodian that may have been obtained during various cases and/or matters; the hyperlink shows the custodian record across all cases, including the information retrieved from the Unified Directory 122. Thus, all of the information regarding the custodian does not need to be copied or manually input to the case record. This is particularly advantageous where a single custodian is assigned to multiple cases. Rather, according to embodiments of the present invention, the electronic discovery management server 110, upon a particular collection being initialized, may access the Unified Directory 122 in order to determine the information about the particular custodian, including the data storage locations that the custodian uses, such as workstations, HomeSpaces, email and shared drives, and use that information to automatically begin the collection process.

Figure 19:
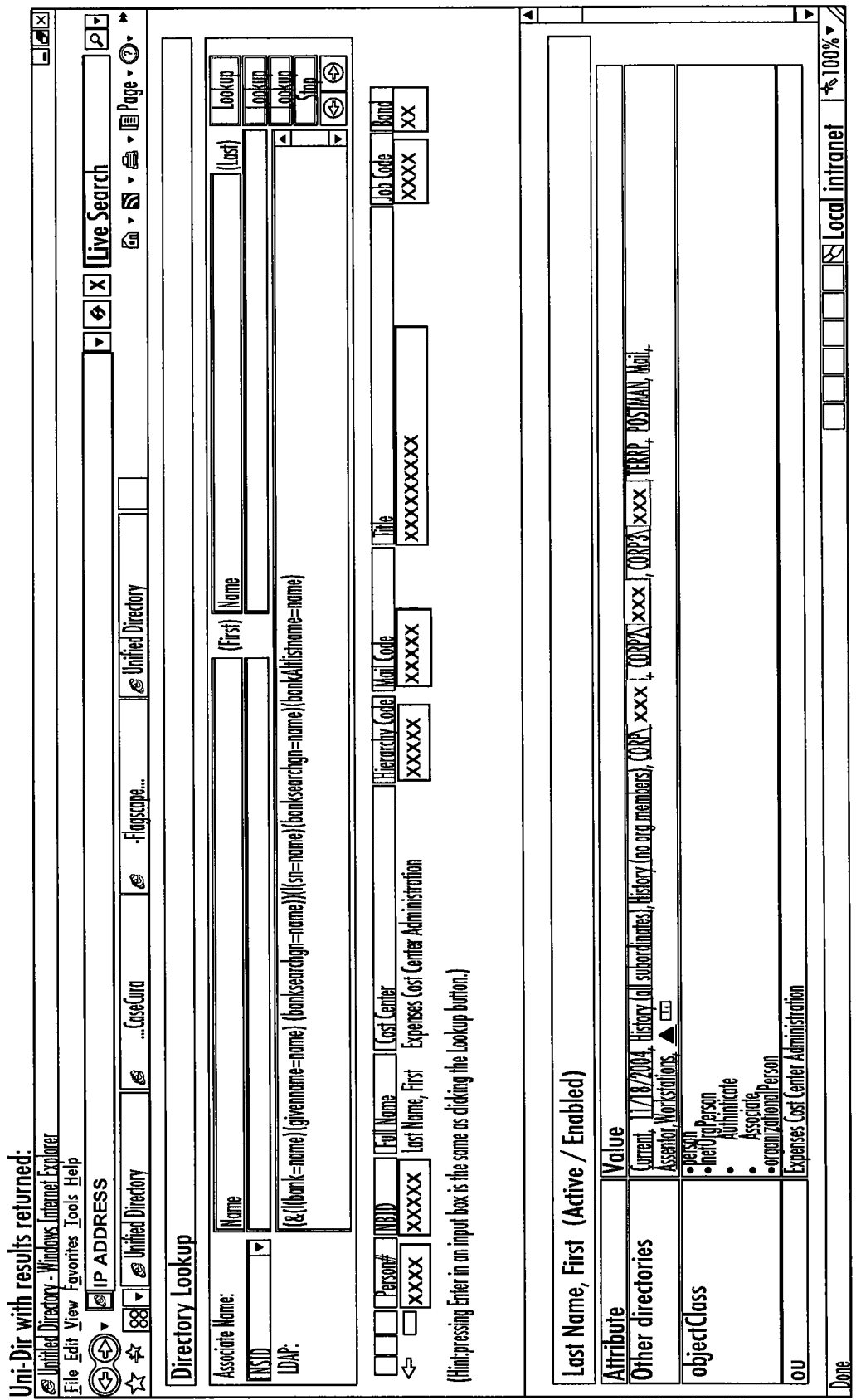

Referring to FIG. 19, a screen shot of the custodian profile within the Unified Directory 122 is provided. As shown, the Unified Directory 122 may be queried with particular information about one or more custodian(s), for example, name or email address, and the matching results will be provided. This would occur, for example, when custodians are added to cases, as discussed in detail above. Furthermore, if the e-discovery manager is within the case record and viewing the custodian page of the case record, as illustrated in FIG. 18, the hyperlinks provided in the custodian names set forth in the custodian list will allow the e-discovery manager to access a page very similar to this one, except that the Directory Lookup feature will not appear. Rather, activating that hyperlink in the case record will bring the e-discovery manager to the custodian profile, where the information about the custodian and his or her data storage locations may be reviewed. Thus, these screen shots demonstrate how custodians are managed and stored separately from the cases with which they may be associated according to some embodiments of the present invention.

Figure 20:
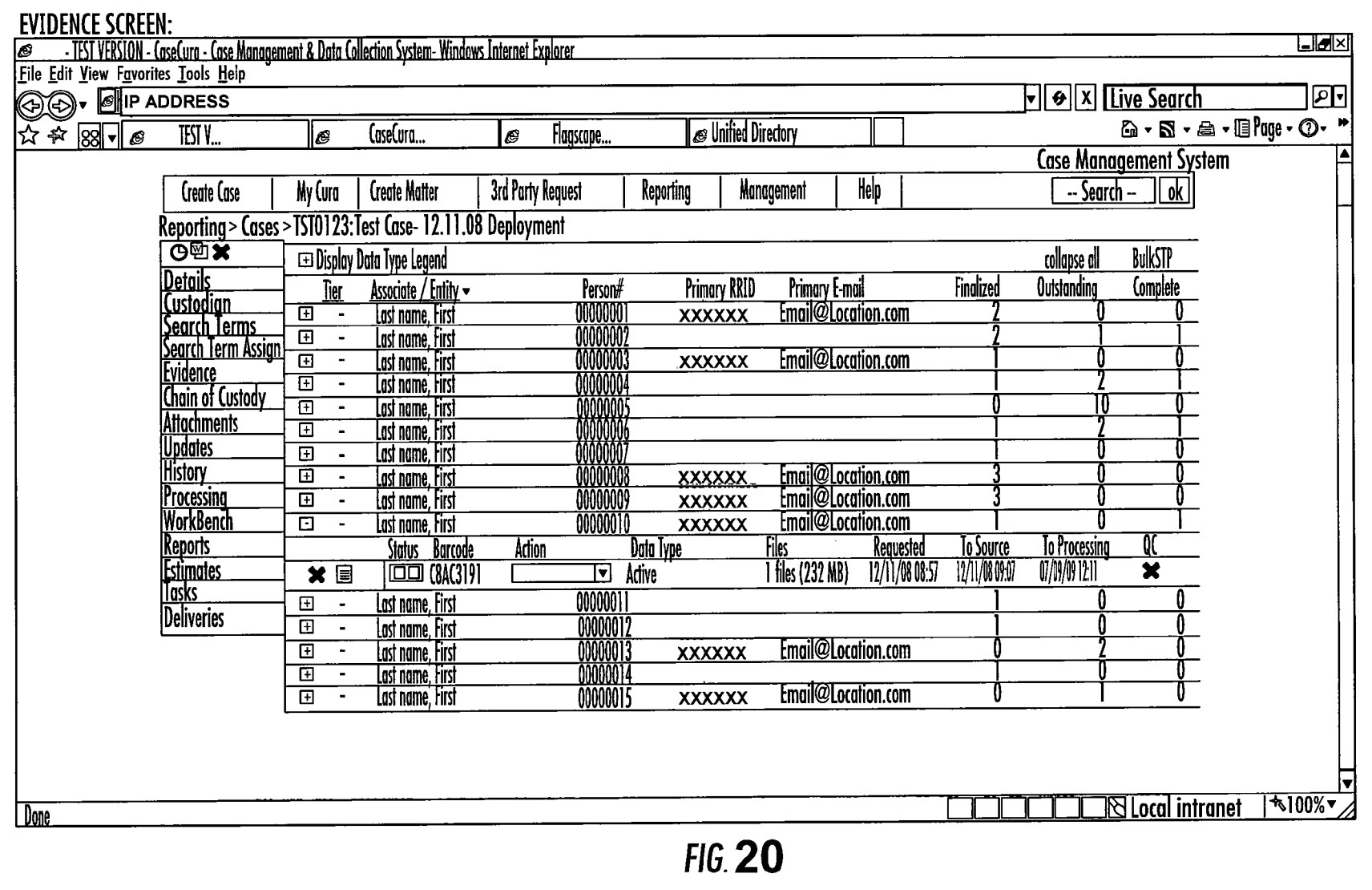

Referring now to FIG. 20, a screen shot of the evidence page within the case record is shown. As discussed previously, evidence metadata, like custodian information, is stored separately from the case record and linked to the cases and/or custodians to which it relates. This allows the data collected for one custodian in a particular case to be readily accessed and used in another case. As shown in FIG. 20, a list is provided within the case record that sets forth all custodians from whom data has been collected or identified for use within that specific case. Furthermore, the list of the custodian names contain hyperlinks to the custodians' profiles within the Unified Directory 122 and/or the custodian record across all cases (according to different embodiments), which profile or record houses a full list of the barcodes associated with data historically collected from that custodian. Thus, from the case record, it is possible, according to some embodiments of the present invention, to readily access both a list of all collections that have been performed for that specific case, and, through activating one hyperlink, a list of all collections that have been performed with respect to a particular custodian.

In that regard, referring now to FIG. 21, a screen shot showing the list of barcodes associated with a particular custodian within the Unified Directory 122 is shown. Thus, the list includes all data collected from the custodian, for any number of cases. As discussed previously, this list may be used to access the data at any time, even if the e-discovery manager is working on an entirely separate case. This reduces the instances of over-collection and wasted effort and storage space by promoting the sharing of data among cases. The screen shots provided and the processes described merely depict one embodiment of the present invention. It should be appreciated that there will be numerous ways to implement the novel concept of structuring the electronic discovery system such that the case, custodian, and collected data management processes are separate.

Thus, present embodiments herein disclosed provide for automated straight-through processing in an electronic discovery system. Further, the embodiments described herein provide for electronic discovery processes, such as, but not limited to, data collection, barcoding, source-to-processing, quality control, third-party network data transfer and data analysis platform loading to be automatically initiated and performed in pipeline fashion. Once a process is completed on a dataset, the next process in the flow is automatically initiated unless exceptions are determined to exist. In addition, embodiments provide for prioritizing cases and conducting each process in the straight-through data processing based on the case prioritization.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other updates, combinations, omissions, modifications and substitutions, in addition to those set forth in the above paragraphs, are possible.

Those skilled in the art may appreciate that various adaptations and modifications of the just described embodiments can be configured without departing from the scope and spirit of the invention. Therefore, it is to be understood that, within the scope of the appended claims, the invention may be practiced other than as specifically described herein.

The invention claimed is:

1. A method for providing automatic straight-through data processing in an electronic discovery system, comprising:

receiving, at a computing device, case-defining information for creating a case in the electronic discovery system, wherein electronic discovery includes processes in which electronic data is processed with an intent of using the electronic data as evidence in at least one of a legal proceeding, an audit, a regulatory investigation, or a forensics investigation;

receiving, at a computing device, a request for electronic data associated with the case;

determining, by a computing device processor, collection prioritization for collecting the electronic data from computer network storage locations assigned to custodians associated with the case, wherein collection prioritization is based on a priority assigned to the case and collection associated with high-priority cases are performed on a next-available processing thread and collection associated with low-priority cases and no-priority cases are placed in a processing queue and performed on a first-in, first-out basis;

based on the collection prioritization, automatically initiating, by a computing device processor, collection of the electronic data from the computer network storage locations;

determining, by a computing device processor, coding prioritization for label-coding of the collected electronic data, wherein coding prioritization is based on a priority assigned to the case and label-coding associated with high-priority cases are performed on a next-available processing thread and label-coding associated with low-priority cases and no-priority cases are placed in a processing queue and performed on a first-in, first-out basis;

in response to verifying successful completion of collection of the electronic data and based on the coding prioritization, automatically initiating, by a computing device processor, label-coding of the collected electronic data;

determining, by a computing device processor, formatting prioritization for formatting the collected and labeled electronic data, wherein formatting prioritization is based on a priority assigned to the case and formatting associated with high-priority cases are performed on a next-available processing thread and formatting associated with low-priority cases and no-priority cases are placed in a processing queue and performed on a first-in, first-out basis;

in response to verifying successful completion of label-coding of the collected electronic data and based on the formatting prioritization, automatically initiating, by a computing device processor, formatting of the collected and labeled electronic data;

determining, by a computing device processor, quality control prioritization for performing quality control processing on the collected electronic data, wherein quality control prioritization is based on a priority assigned to the case and quality control processing associated with high-priority cases are performed on a next-available processing thread and quality control processing associated with low-priority cases and no-priority cases are placed in a processing queue and performed on a first-in, first-out basis; and in response to verifying successful completion of formatting of the collected electronic data and based on the quality control prioritization, automatically initiating, by a computing device processor, quality control processing of the electronic data.

2. The method of claim 1, further comprising, in response to verifying successful completion of the quality control processing, automatically initiating third-party network transfer of the electronic data.

3. The method of claim 2, further comprising determining by a computing device processor, transfer prioritization for the automated third-party network transfer of the electronic data, wherein the transfer prioritization is based on a priority assigned to the case.

4. The method of claim 1, further comprising, in response to verifying successful completion of the quality control processing, automatically initiating analysis platform loading of the electronic data.

5. The method of claim 4, further comprising determining by a computing device processor, platform loading prioritization for the automated analysis platform loading of the electronic data, wherein the transfer prioritization is based on a priority assigned to the case.

6. The method of claim 1, wherein the collection prioritization, the coding prioritization, the formatting prioritization and the quality control are based on one or more of case client, age of the case, monetary risk of the case, reputational risk of the case or client-defined case categorization.

7. An apparatus for automated straight-through processing in an electronic discovery system, the apparatus comprising:

a computing processor including a memory and at least one processor; and an electronic discovery data processing module stored in the memory, executable by the processor and configured to:

in response to a request for electronic data associated with a case in the electronic discovery system, determine collection prioritization for collecting electronic data from computer network storage locations assigned to custodians associated with the case, wherein collection prioritization is based on a priority assigned to the case and collection associated with high-priority cases are performed on a next-available processing thread and collection associated with low-priority cases and no-priority cases are placed in a processing queue and performed on a first-in, first-out basis;

based on the collection prioritization, automatically initiate collection of the electronic data from the;

determine coding prioritization for label-coding of the collected electronic data, wherein coding prioritization is based on a priority assigned to the case and label-coding associated with high-priority cases are performed on a next-available processing thread and label-coding associated with low-priority cases and no-priority cases are placed in a processing queue and performed on a first-in, first-out basis;

in response to verifying successful completion of collection of the electronic data and based on the coding prioritization, automatically initiate label-coding of the collected electronic data;

determine formatting prioritization for formatting the collected and labeled electronic data, wherein formatting prioritization is based on a priority assigned to the case and formatting associated with high-priority cases are performed on a next-available processing thread and formatting associated with low-priority cases and no-priority cases are placed in a processing queue and performed on a first-in, first-out basis;

in response to verifying successful completion of label-coding of the collected electronic data and based on the formatting prioritization, automatically initiate formatting of the collected and labeled electronic data;

determine quality control prioritization for performing quality control processing on the collected electronic data, wherein quality control prioritization is based on a priority assigned to the case and quality control processing associated with high-priority cases are performed on a next-available processing thread and quality control processing associated with low-priority cases and no-priority cases are placed in a processing queue and performed on a first-in, first-out basis; and in response to verifying successful completion of formatting of the collected electronic data and based on the quality control prioritization, automatically initiate quality control processing of the electronic data, wherein the electronic data is processed with an intent of securing the electronic data as evidence in at least one of a legal proceeding, an audit, a regulatory investigation, or a forensics investigation.

8. The apparatus of claim 7, wherein the electronic discovery data processing module is further configured to, in response to verifying successful completion of the quality control processing, automatically initiate third-party network transfer of the electronic data.

9. The apparatus of claim 8, wherein the electronic discovery data processing module is further configured to determine transfer prioritization for the automated third-party network transfer of the electronic data, wherein the transfer prioritization is based on a priority assigned to the case.

10. The apparatus of claim 7, wherein the electronic discovery data processing module is further configured to, in response to verifying successful completion of the quality control processing, automatically initiate third-party network transfer of the electronic data.

11. The apparatus of claim 10, wherein the electronic discovery data processing module is further configured to determine transfer prioritization for the automated third-party network transfer of the electronic data, wherein the transfer prioritization is based on a priority assigned to the case.

12. The apparatus of claim 7, wherein the collection prioritization, the coding prioritization, the formatting prioritization and the quality control prioritization are based on one or more of case client, age of the case, monetary risk of the case, reputational risk of the case or client-defined case categorization.

13. A computer program product comprising:

a non-transitory computer-readable medium comprising:

a first set of codes for causing a computer to receive case-defining information for creating a case the electronic discovery system, wherein electronic discovery includes processes in which electronic data is processed with an intent of using the electronic data as evidence in at least one of a legal proceeding, an audit, a regulatory investigation, or a forensics investigation;

a second set of codes for causing a computer to receive a request for electronic data associated with the case;

a third set of codes for causing a computer to determine collection prioritization for collecting electronic data from computer network storage locations assigned to custodians associated with the case, wherein collection prioritization is based on a priority assigned to the case and collection associated with high-priority cases are performed on a next-available processing thread and collection associated with low-priority cases and no-priority cases are placed in a processing queue and performed on a first-in, first-out basis;

a fourth set of codes for causing a computer to, based on the collection prioritization, automatically initiate collection of the electronic data from the computer network storage locations;

a fifth set of codes for causing a computer to determine coding prioritization for label-coding of the collected electronic data, wherein coding prioritization is based on a priority assigned to the case and label-coding associated with high-priority cases are performed on a next-available processing thread and label-coding associated with low-priority cases and no-priority cases are placed in a processing queue and performed on a first-in, first-out basis;

a sixth set of codes for causing a computer to, in response to verifying successful completion of collection of the electronic data and based on the coding prioritization, automatically initiate label-coding of the collected electronic data;

a seventh set of codes for causing a computer to determine formatting prioritization for formatting the collected and labeled electronic data, wherein formatting prioritization is based on a priority assigned to the case and formatting associated with high-priority cases are performed on a next-available processing thread and formatting associated with low-priority cases and no-priority cases are placed in a processing queue and performed on a first-in, first-out basis;

an eighth set of codes for causing a computer to, in response to verifying successful completion of label-coding of the collected electronic data and based on the formatting prioritization, automatically initiate formatting of the collected and labeled electronic data;

a ninth set of codes for causing a computer to determine quality control prioritization for performing quality control processing on the collected electronic data, wherein quality control prioritization is based on a priority assigned to the case and quality control processing associated with high-priority cases are performed on a next-available processing thread and quality control processing associated with low-priority cases and no-priority cases are placed in a processing queue and performed on a first-in, first-out basis; and a tenth set of codes for causing a computer to, in response to verifying successful completion of formatting of the collected electronic data and based on the quality control prioritization, automatically initiate quality control processing of the electronic data.

14. The computer program product of claim 13, wherein the collection prioritization, the coding prioritization, the formatting prioritization and the quality control prioritization are based on one or more of case client, age of the case, monetary risk of the case, reputational risk of the case or client-defined case categorization.

15. The computer program product of claim 13, further comprising an eleventh set of codes for causing a computer to, in response to verifying successful completion of the quality control processing, automatically initiate third-party network transfer of the electronic data.

16. The computer program product of claim 15, further comprising a twelfth set of codes for causing a computer to determine transfer prioritization for the automated third-party network transfer of the electronic data, wherein the transfer prioritization is based on a priority assigned to the case.

17. The computer program product of claim 13, further comprising an eleventh set of codes for causing a computer to, in response to verifying successful completion of the quality control processing, automatically initiating analysis platform loading of the electronic.

18. The computer program product of claim 17, further comprising a twelfth set of codes for causing a computer to determine platform loading prioritization for the automated analysis platform loading of the electronic data, wherein the transfer prioritization is based on a priority assigned to the case.

* * * * *